US006455073B1

(12) United States Patent
Meredith et al.

(10) Patent No.: US 6,455,073 B1
(45) Date of Patent: Sep. 24, 2002

(54) COVALENT MICROPARTICLE-DRUG CONJUGATES FOR BIOLOGICAL TARGETING

(75) Inventors: Michael J. Meredith, Lake Oswego; Milton B. Yatvin, Portland, both of OR (US); Richard L. Pederson, San Gabriel, CA (US)

(73) Assignee: Enzrel, Inc., Portland, OR (US)

( * ) Notice: Subject to any disclaimer, the term of this patent is extended or adjusted under 35 U.S.C. 154(b) by 0 days.

(21) Appl. No.: 09/612,732

(22) Filed: Jul. 10, 2000

(51) Int. Cl.$^7$ .............. A61K 9/14; A61K 9/16; A61K 9/50; A61K 9/52; A61K 9/56
(52) U.S. Cl. .............. 424/490; 424/489; 424/491
(58) Field of Search .................. 424/480, 489, 424/490, 491

(56) References Cited

U.S. PATENT DOCUMENTS

| | | |
|---|---|---|
| 4,744,989 A | 5/1988 | Payne et al. |
| 4,793,986 A | 12/1988 | Serino et al. |
| 4,874,240 A | 10/1989 | Watts et al. |
| 4,921,757 A | 5/1990 | Wheatley et al. |
| 4,963,526 A | 10/1990 | Ecanow et al. |
| 5,004,611 A | 4/1991 | Leigh |

(List continued on next page.)

FOREIGN PATENT DOCUMENTS

| | | |
|---|---|---|
| EP | 350287 | 1/1990 |
| EP | 855179 | 1/1997 |
| WO | WO8902733 | 4/1989 |
| WO | WO9300910 | 1/1993 |
| WO | WO953035 | 2/1995 |

Primary Examiner—Thurman K. Page
Assistant Examiner—Rachel M. Bennett

(74) Attorney, Agent, or Firm—McDonnell Boehnen Hulbert & Berghoff

(57) ABSTRACT

This invention provides reagents and methods for specifically delivering antibiotic, antimicrobial and antiviral compounds, drugs and agents to phagocytic mammalian cells. The invention also relates to specific delivery to and uptake of such compounds by phagocytic cells. The invention specifically relates to reagents and methods for facilitating the entry of antibiotic, antimicrobial and antiviral compounds, drugs and agents into phagocytic cells. The invention specifically provides compositions of matter and pharmaceutical embodiments of such compositions comprising such antibiotic, antimicrobial or antiviral compounds, drugs and agents conjugated to, impregnated with or coated onto particulate carriers generally termed microparticles. In particular embodiments, the antibiotic, antimicrobial and antiviral compounds, drugs and agents are covalently linked to a microparticle via a specifically-degradable linker molecule which is the target of a microorganism-specific protein having enzymatic activity. Also provided are porous microparticles impregnated with antibiotic, antimicrobial or antiviral compounds, drugs and agents wherein the surface or outside extent of the microparticle is covered with a degradable coating that is specifically degraded within an infected phagocytic mammalian cell. Also provided are nonporous microparticles coated with antibiotic, antimicrobial or antiviral compounds, drugs and agents and further coated wherein the surface or outside extent of the microparticle is covered with a degradable coating that is specifically degraded within an infected phagocytic mammalian cell. Thus, the invention provides cell targeting of drugs wherein the targeted drug is only released in cells infected with a particular microorganism. Methods of inhibiting, attenuating, arresting, combating and overcoming microbial infection of phagocytic mammalian cells in vivo and in vitro, especially cells infected with tuberculosis-causing and other Mycobacterium species microorganisms, are also provided.

12 Claims, 17 Drawing Sheets

U.S. PATENT DOCUMENTS

| | | |
|---|---|---|
| 5,043,165 A | 8/1991 | Radhakrishnan |
| 5,053,217 A | 10/1991 | Lehigh |
| 5,053,394 A | 10/1991 | Ellestacl et al. |
| 5,141,674 A | 8/1992 | Leigh |
| 5,223,263 A | 6/1993 | Hostetler et al. |
| 5,258,453 A | 11/1993 | Kopecek et al. |
| 5,466,468 A | 11/1995 | Schneider et al. |
| 5,484,809 A | 1/1996 | Hostetler et al. |
| 5,543,390 A | 8/1996 | Yatkin et al. |
| 5,543,391 A | 8/1996 | Yatkin et al. |
| 5,580,571 A | 12/1996 | Hostetler et al. |
| 5,610,163 A | 3/1997 | Banholzer et al. |
| 5,626,869 A | 5/1997 | Nygvist et al. |
| 5,635,206 A | 6/1997 | Ganter et al. |
| 5,648,392 A * | 7/1997 | Sacchettini et al. ........... 514/60 |
| 5,654,314 A | 8/1997 | Banholzer et al. |
| 5,665,379 A | 9/1997 | Herslof et al. |
| 5,744,461 A | 4/1998 | Hostetler et al. |
| 5,744,592 A | 4/1998 | Hostetler et al. |
| 5,756,116 A | 5/1998 | Hostetler et al. |
| 5,762,904 A | 6/1998 | Okada et al. |
| 5,770,738 A | 6/1998 | Banholzer et al. |
| 5,840,674 A * | 11/1998 | Yatvin et al. .................. 514/2 |
| 5,843,509 A | 12/1998 | Calvo Salve et al. |
| 5,955,451 A | 9/1999 | Lichtenberger et al. |
| 5,958,450 A | 9/1999 | Tashiro et al. |
| 6,015,576 A | 1/2000 | See et al. |
| 6,060,082 A | 5/2000 | Chen et al. |
| 6,117,449 A | 9/2000 | See et al. |
| 6,207,185 B1 | 3/2001 | See et al. |
| 6,231,888 B1 | 5/2001 | Lerner et al. |

* cited by examiner

Synthesis of Inhibitor C6

Urease-Catalyzed Release of Drug from Polymer-Coated Microparticles

Synthesis of Carbamate Derivatized Polymer Coating

Carbamate-Derivatized Polymer Coating

COVALENT MICROPARTICLE-DRUG CONJUGATES FOR BIOLOGICAL TARGETING

BACKGROUND OF THE INVENTION

This invention was made with government support under grant 1-R01-CA49416 by the National Institutes of Health. The government has certain rights in the invention.

1. Field of the Invention

This invention relates to reagents and methods for facilitating the entry of biologically-active compounds into phagocytic cells. The invention specifically provides particulate carriers generally termed microparticles comprising antimicrobial compounds, both per se as compositions of matter and as pharmaceutical compositions thereof. Alternative embodiments of said microparticle carriers are provided wherein one or a multiplicity of antimicrobial compounds are linked to a microparticle via a specifically-cleaved linker moiety, or wherein a porous microparticle is impregnated with one or a multiplicity of antimicrobial compounds, or wherein the microparticle is coated with one or a multiplicity of antimicrobial compounds, wherein the impregnated or coated microparticle is further coated with a specifically-degradable coating material, wherein in their respective embodiments the specifically-cleaved linker moiety and the specifically-degradable coating material are the targets of a microorganism-specific protein having an enzymatic activity not otherwise expressed in the phagocytic cell, or that is specifically expressed by the phagocytic cell only when infected with said microorganism. Thus, the invention provides cell targeting of drugs to phagocytic cells wherein the targeted drug is only released in phagocytic cells that infected with a particular microorganism. Methods of treating diseases having an intracellular microbial etiology are also provided, particularly for the treatment of tuberculosis and other Mycobacterium-caused diseases.

2. Background of the Related Art

A major goal in the pharmacological arts has been the development of reagents and methods for facilitating specific delivery of therapeutic compounds, drugs and other agents to the appropriate cells and tissues that would benefit from such treatment, and the avoidance of the general physiological effects of systemic or otherwise inappropriate delivery of such compounds, drugs or agents to other cells or tissues of the body. The most common example of the need for such specificity is in the field of antibiotic therapy, in which the amount of a variety of antibiotic, antimicrobial and antiviral compounds, drugs and agents that can be safely administered to a patient is limited by their cytotoxic and immunogenic effects.

It is also recognized in the medical arts that certain cells are the sites of pharmacological action of certain compounds, drugs or agents or are involved in the biological response to certain stimuli. In particular, it is now recognized that certain cell types are reservoirs for occult infection that evades normal immune surveillance and permits the persistence of a chronically infected disease state. Specific delivery of diagnostic or therapeutic compounds, drugs or agents to such cells is thus desirable to increase the specificity and effectiveness of clinical diagnostic or therapeutic techniques.

A. Drug Targeting

It is desirable to increase the efficiency and specificity of administration of a therapeutic compound, drug or agent to the cells of the relevant tissues in a variety of pathological states. This is particularly important as relates to antibiotic, antimicrobial and antiviral compounds, drugs or agents. These compounds, drugs or agents typically have pleiotropic antibiotic, immunogenic, cytopathic and cytotoxic effects that damage or destroy uninfected cells as well as infected cells. In addition, certain compounds, drugs or agents are "activated" or chemically modified by an enzymatic or chemical activity specific for infected cells, in which activated form the compounds, drugs or agents are particularly toxic. Resistance to these types of compounds, drugs or agents can arise by attenuation, mutation or ablation of the chemical or enzymatic activity in the infected cell. Thus, an efficient delivery system which would enable the delivery of such compounds, drugs or agents, particularly said "activated" forms thereof, specifically to infected cells would increase the efficacy of treatment, overcome drug resistance, reduce the associated "side effects" of such drug treatments, and also serve to reduce morbidity and mortality associated with clinical administration of such compounds, drugs or agents.

Numerous methods for enhancing the cytotoxic activity and the specificity of antibiotic drug action have been proposed. One method, receptor targeting, involves linking the therapeutic agent to a ligand which has an affinity for a receptor expressed on the desired target cell surface. Using this approach, antibiotic, antimicrobial and antiviral compounds, drugs and agents are intended to adhere to the target cell following formation of a ligand-receptor complex on the cell surface. Entry into the cell could then follow as the result of internalization of ligand-receptor complexes. Following internalization, the antibiotic, antimicrobial and antiviral compounds, drugs and agents may then exert therapeutic effects directly on the cell.

The ligand-receptor approach is plagued by a number of biological limitations. Receptor-mediated uptake does not specifically target infected cells; all cells that happen to express the receptor take up the drug. A further limitation of the receptor targeting approach lies in the fact that there are only a finite number of receptors on the surface of target cells. It has been estimated that the maximum number of receptors on a cell is approximately one million (Darnell et al., 1990, *Molecular Cell Biology*, 2d ed., W. H. Freeman: New York). This estimate predicts that there may be a maximum one million drug-conjugated ligand-receptor complexes on any particular cell. Since not all of the ligand-receptor complexes may be internalized, and any given ligand-receptor system may express many-fold fewer receptors on any particular cell surface, the efficacy of intracellular drug delivery using this approach is uncertain. Other known intracellular ligand-receptor complexes (such as the steroid hormone receptor) express as few as ten thousand hormone molecules per cell, and thus are even less suitable for mediating cell-specific targeting of antibiotic, antibiotic or antiviral compounds, drugs and agents. Id. Finally, once the bound drug entered a cell, it would not be expected to be differentially released in infected cells.

Other methods of delivering therapeutic agents at concentrations higher than those achievable through the receptor targeting process include the use of lipid conjugates that have selective affinities for specific biological membranes. These methods have met with little success (see, for example, Remy et al., 1962, *J Org. Chem.* 27: 2491–2500; Mukhergee & Heidelberger, 1962, *Cancer Res.* 22: 815–22; Brewster et al., 1985, *J. Pharm. Sci.* 77: 981–985).

Liposomes have been used to attempt cell targeting. U.S. Pat. No. 5,223,263, issued Jun. 29, 1993 to Hostetler et al. disclose conjugates between antiviral nucleoside analogues and polar lipids.

U.S. Pat. No. 5,484,809, issued Jan. 16, 1996 to Hostetler et al. disclose taxol and taxol derivatives conjugated to phospholipids.

U.S. Pat. No. 5,580,571, issued Dec. 3, 1996 to Hostetler et al. disclose nucleoside analogues conjugated to phospholipids.

U.S. Pat. No. 5,744,461, issued Apr. 28, 1998 to Hostetler et al. disclose nucleoside analogues conjugated to phosphonoacetic acid lipid derivatives.

U.S. Pat. No. 5,744,592, issued Apr. 28, 1998 to Hostetler et al. disclose nucleoside analogues conjugated to phospholipids.

U.S. Pat. No. 5,756,116, issued May 26, 1998 to Hostetler et al. disclose nucleoside analogues conjugated to phospholipids.

International Patent Application Publication Number WO89/02733, published April 1989 to Vical disclose conjugates between antiviral nucleoside analogues and polar lipids.

European Patent Application Publication Number 0350287A2 to Vical disclose conjugates between antiviral nucleoside analogues and polar lipids.

International Patent Application Publication Number WO93/00910 to Vical disclose conjugates between antiviral nucleoside analogues and polar lipids.

Rahman et al., 1982, *Life Sci.* 31: 2061–71 found that liposomes which contained galactolipid as part of the lipid appeared to have a higher affinity for parenchymal cells than liposomes which lacked galactolipid.

Gregoriadis, 1995, *Trends in Biotechnology* 13: 527–537 reviews the "progress and problems" associated with using liposomes for targeted drug delivery.

Ledley, 1995, *Human Gene Therapy* 6: 1129–1144 reviews the use of liposomes for gene therapy.

Mickisch, 1995, *World J. Urology* 13: 178–185 reviews the use of liposomes for gene therapy of renal cell carcinoma.

Yang et al. 1997, *J. Neurotrauma* 14: 281–297 review the use of cationic liposomes for gene therapy directed to the central nervous system.

Storm & Crommelin, 1997, *Hybridoma* 16: 119–125 review the preliminary use of liposomes for targeting chemotherapeutic drugs to tumor sites.

Manusama et al., 1998, *Semin. Surg. Oncol.* 14: 232–237 reported on preclinical and clinical trials of liposome-encapsulated tumor necrosis factor for cancer treatments.

To date, however, efficient or specific drug delivery has not been predictably achieved using drug-encapsulated liposomes.

Drug delivery to specific sites or cells has been attempted as a way to enhance drug effectiveness. In one example of this approach, prodrug activation has been attempted using antibodies to provide "time-released" drug delivery agents (Bignami et al., 1992, *Cancer Res.* 52: 5759–5764). In this approach, a specific targeting antibody conjugated with a prodrug-activating enzyme was used to activate a systemically-delivered prodrug only at the specific site recognized by the antibody.

There remains a need for the development of cell-specific drug targeting and delivery systems, particularly with antibiotic, antimicrobial and antiviral compounds, drugs and agents.

B. Phagocytic Cell-Specific Targeting

Cell-specific targeting is an important goal of antimicrobial therapy, particularly in the event that a specific cell type is a target of acute or chronic infection. Targeting a specific infected cell type would be advantageous because it would allow administration of antibiotic, antimicrobial or antiviral compounds, drugs or agents to an animal suffering from infection with a microbial pathogen, without the risk of non-specific toxicity to uninfected cells that would exist with nontargeted administration of toxic compounds, and because it would permit administration of dosages unattainable using systemically-administered, non-targeted embodiments of such antibiotic, antiviral and antimicrobial compounds, drugs and agents. This is particularly true of "activated" compounds, drugs or agents, which are by definition particularly toxic forms of said compounds, drugs or agents and particularly efficient in their antibiotic, antimicrobial, or antiviral properties. An additional advantage of such targeted antimicrobial therapy would be improved pharmacokinetics that would result from specific concentration of antibiotic, antimicrobial or antiviral compounds, drugs and agents to the infected cells that are the sites of infection.

Phagocytic cells such as monocytes and macrophages are known to be specific targets for infection of certain pathogenic microorganisms.

Sturgill-Koszycki et al., 1994, *Science* 263: 678–681 disclose that the basis for lack of acidification of phagosomes in *M. avium* and *M. tuberculosis*-infected macrophages is exclusion of the vesicular proton-ATPase.

Sierra-Honigman et al., 1993, *J. Neuroimmunol.* 45: 31–36 disclose Borna disease virus infection of monocytic cells in bone marrow.

Maciejewski et al., 1993, *Virol.* 195: 327–336 disclose human cytomegalovirus infection of mononucleated phagocytes in vitro.

Alvarez-Dominguez et al., 1993, *Infect. Immun.* 61: 3664–3672 disclose the involvement of complement factor C1q in phagocytosis of *Listeria monocytogenes* by macrophages.

Kanno et al., 1993, *J. Virol.* 67: 2075–2082 disclose that Aleutian mink disease parvovirus replication depends on differentiation state of the infected macrophage.

Embretson et al., 1993, *Nature* 362: 359–362 disclose covert infection of macrophages by human immunodeficiency virus.

Meltzer & Gendelman, 1992, *Curr. Top. Microbiol. Immunol.* 181: 239–263 disclose infection of mononuclear phagocytes with human immunodeficiency virus.

Kanno et al., 1992, *J. Virol.* 66: 5305–5312 disclose that Aleutian mink disease parvovirus infects peritoneal macrophages in mink.

Narayan et al., 1992, *J. Rheumatol.* 32: 25–32 disclose arthritis in animals caused by infection of macrophage precursors with lentivirus, and activation of quiescent lentivirus infection upon differentiation of such precursor cells into terminally-differentiated macrophages.

Horwitz, 1992, *Curr. Top. Microbiol. Immunol.* 181: 265–282 disclose *Legionella pneumophila* infections of alveolar macrophages as the basis for Legionnaire's disease and Pontiac fever.

Sellon et al., 1992, *J. Virol.* 66: 5906–5913 disclose that equine infectious anemia virus replicates in tissue macrophages in vivo.

Groisman et al., 1992, *Proc. Natl. Acad. Sci. USA* 89: 11939–11943 disclose that *S. typhimurium* survives inside infected macrophages by resistance to antibacterial peptides.

Friedman et al., 1992, *Infect. Immun.* 60: 4578–4585 disclose *Bordetella pertussis* infection of human macrophages.

Stellrecht-Broomhall, 1991, *Viral Immunol.* 4: 269–280 disclose that lymphocytic choriomeningitis virus infection of macrophages promotes severe anemia caused by macrophage phagocytosis of red blood cells.

Frehel et al., 1991, *Infect. Immun.* 59: 2207–2214 disclose infection of spleen and liver-specific inflammatory macrophages by *Mycobacterium avium*, the existence of the microbe in encapsulated phagosomes within the inflammatory macrophages and survival therein in phagolysosomes.

Bromberg et al., 1991, *Infect. Immun.* 59: 4715–4719 disclose intracellular infection of alveolar macrophages.

Mauel, 1990, *J. Leukocyte Biol.* 47: 187–193 disclose that Leishmania spp. are intracellular parasites in macrophages.

Buchmeier and Heffron, 1990, *Science* 248: 730–732 disclose that *Salmonella typhimurium* infection of macrophages induced bacterial stress proteins.

Panuska et al., 1990, *J. Clin. Invest.* 86: 113–119 disclose productive infection of alveolar macrophages by respiratory syncytial virus.

Cordier et al., 1990, *Clin. Immunol. Immunopathol.* 55: 355–367 disclose infection of alveolar macrophages by visna-maedi virus in chronic interstitial lung disease in sheep.

Schlessinger and Horwitz, 1990, *J. Clin. Invest.* 85: 1304–1314 disclose *Mycobacterium leprae* infection of macrophages.

Schmidt et al., 1990, *Res. Virol.* 141: 143–152 disclose infection of primary cultures of liver Kupffer cells with human immunodeficiency virus.

Clarke et al., 1990, *AIDS* 4: 1133–1136 disclose human immunodeficiency virus infection of alveolar macrophages in lung.

Baroni et al., 1988, *Am. J. Pathol.* 133: 498–506 disclose human immunodeficiency virus infection of lymph nodes.

Payne et al, 1987, *J. Exp. Med.* 166: 1377–1389 disclose *Mycobacterium tuberculosis* infection of macrophages.

Murray et al., 1987, *J. Immunol.* 138: 2290–2296 disclose that liver Kupffer cells are the initial targets for *L. donovani* infection.

Koenig et al., 1986, *Science* 233: 1089–1093 disclose human immunodeficiency virus infection of macrophages in the central nervous system.

Gendelman et al., 1985, *Proc. Natl. Acad. Sci. USA* 82: 7086–7090 disclose infection of phagocytic cells with lentivirus.

Horwitz and Maxfield, 1984, *J. Cell Biol.* 99: 1936–1943 disclose that *L. pneumophila* survives in infected phagocytic cells at least in part by inhibiting reduction of intraphagosomic hydrogen ion concentration (pH).

Shanley and Pesanti, 1983, *Infect. Immunol.* 41: 1352–1359 disclose cytomegalovirus infection of macrophages in murine cells.

Horwitz, 1983, *J. Exp. Med.* 158: 2108–2126 disclose that *L. pneumophila* is an obligate intracellular parasite that is phagocytized into a phagosome wherein fusion with lysosome is inhibited.

Chang, 1979, *Exp. Parasitol.* 48: 175–189 disclose *Leishmania donovani* infection of macrophages.

Wyrick and Brownridge, 1978, *Infect. Immunol.* 19: 1054–1060 disclose *Chlamydia psittaci* infection of macrophages.

Halstead et al., 1977, *J. Exp. Med.* 146: 201–217 disclosed infection of phagocytic cells with dengue virus.

Nogueira and Cohn, 1976, *J. Exp. Med.* 143: 1402–1420 disclose *Trypanosoma cruzi* infection of macrophages.

Jones and Hirsch, 1972, *J. Exp. Med.* 136: 1173–1194 disclose *Toxoplasma gondii* infection of macrophages.

Persistent infection of phagocytic cells has been reported in the prior art.

Embretson et al., 1993, *Nature* 362: 359–361 disclose covert infection of macrophages with HIV and dissemination of infected cells throughout the immune system early in the course of disease.

Schnorr et al., 1993, *J. Virol.* 67: 4760–4768 disclose measles virus persistent infection in vitro in a human monocytic cell line.

Meltzer and Gendelman, 1992, *Curr. Topics Microbiol. Immunol.* 181: 239–263 provide a review of HIV infection of tissue macrophages in brain, liver, lung, skin, lymph nodes, and bone marrow, and involvement of macrophage infection in AIDS pathology.

Blight et al., 1992, *Liver* 12: 286–289 disclose persistent infection of liver macrophages (Kuppfer cells) by hepatitis C virus.

McEntee et al., 1991, *J. gen. Virol.* 72: 317–324 disclose persistent infection of macrophages by HIV resulting in destruction of T lymphocytes by fusion with infected macrophages, and that the macrophages survive fusion to kill other T lymphocytes.

Kondo et al., 1991, *J. gen. Virol.* 72: 1401–1408 disclose latent infection by herpes simplex virus 6 of monocytes activated by differentiation into macrophages.

King et al., 1990, *J. Virol.* 64: 5611–5616 disclose persistent infection of macrophages with lymphocytic choriomeningitis virus.

Schmitt et al., 1990, *Res. Virol.* 141: 143–152 disclose a role for HIV infection of Kupffer cells as reservoirs for HIV infection.

Gendelman et al., 1985, *Proc. Natl. Acad. Sci. USA* 82: 7086–7090 disclose lentiviral (visna-maedi) infection of bone marrow precursors of peripheral blood monocytes/macrophages that provide a reservoir of latently-infected cells.

Halstead et al., 1977, *J. Exp. Med.* 146: 201–217 disclose that macrophages are targets of persistent infection with dengue virus.

Mauel et al., 1973, *Nature New Biol.* 244: 93–94 disclose that lysis of infected macrophages with sodium dodecyl sulfate could release live microbes.

Attempts at cell-specific drug targeting have been reported in the prior art.

Rubinstein et al., 1993, *Pharm. Res.* 10: 258–263 report colon targeting using calcium pectinate (CaPec)-conjugated drugs, based on degradation of CaPec by colon specific (i.e., microflora-specific) enzymes and a hydrophobic drug incorporated into the insoluble CaPec matrices.

Sintov et al., 1993, *Biomaterials* 14: 483–490 report colon-specific targeting using conjugation of drug to insoluble synthetic polymer using disaccharide cleaved by enzymes made by intestinal microflora, specifically, β-glycosidic linkages comprising dextran.

Franssen et al., 1992, *J. Med. Chem.* 35: 1246–1259 report renal cell/kidney drug targeting using low molecular weight proteins (LMWP) as carriers, using enzymatic/chemical hydrolysis of a spacer molecule linking the drug and LMWP carrier.

Bai et al., 1992, *J. Pharm. Sci.* 81: 113–116 report intestinal cell targeting using a peptide carrier-drug system wherein the conjugate is cleaved by an intestine-specific enzyme, prolidase.

Gaspar et al., 1992, *Ann. Trop. Med. Parasitol.* 86: 41–49 disclose primaquine-loaded polyisohexylcyanoacrylate nanoparticles used to target *Leschmania donovani* infected macrophage-like cells in vitro.

Pardridge, 1992, *NIDA Res. Monograph* 120: 153–168 report opioid-conjugated chimeric peptide carriers for targeting to brain across the blood-brain barrier.

Bai and Amidon, 1992, *Pharm. Res.* 9: 969–978 report peptide-drug conjugates for oral delivery and intestinal mucosal targeting of drugs.

Ashborn et al., 1991, *J. Infect. Dis.* 163: 703–709 disclose the use of CD4-conjugated *Pseudomonas aeruginosa* exotoxin A to kill HIV-infected macrophages.

Larsen et al., 1991, *Acta Pharm. Nord.* 3: 41–44 report enzyme-mediated release of drug from dextrin-drug conjugates by microflora-specific enzymes for colon targeting.

Faulk et al., 1991, *Biochem. Int.* 25: 815–822 report adriamycin-transferrin conjugates for tumor cell growth inhibition in vitro.

Zhang and McCormick, 1991, *Proc. Natl. Acad. Sci. USA* 88: 10407–10410 report renal cell targeting using vitamin B6-drug conjugates.

Blum et al., 1982, *Int. J. Pharm.* 12: 135–146 report polystyrene microspheres for specific delivery of compounds to liver and lung.

Trouet et al., 1982, *Proc. Natl. Acad. Sci. USA* 79: 626–629 report that daunorubicin-conjugated to proteins was cleaved by lysosomal hydrolases in vivo and in vitro.

Shen et al., 1981, *Biochem. Biophys. Res. Commun.* 102: 1048–1052 report pH-labile N-cis-acontinyl spacer moieties.

Monoclonal antibodies have been used in the prior art for drug targeting.

Serino et al, U.S. Pat. No. 4,793,986, issued Dec. 27, 1988, provides platinum anticancer drugs conjugated to polysaccharide (dextrin) carrier for conjugation to monoclonal antibodies for tumor cell targeting.

Bickel et al., 1993, *Proc. Natl. Acad. Sci. USA* 90: 2618–2622 discloses the use of a chimeric protein vector for targeting across blood-brain barrier using an anti-transferrin monoclonal antibody.

Rowlinson-Busza and Epenetos, 1992, *Curr. Opin. Oncol.* 4: 1142–1148 provides antitumor immunotargeting using toxin-antibody conjugates.

Blakey, 1992, *Acta Oncol.* 31: 91–97 provides a review of antitumor antibody targeting of antineoplastic drugs.

Senter et al., 1991, in *Immunobiology of Peptides and Proteins*, Vol. VI, pp.97–105 discloses monoclonal antibodies linked to alkaline phosphatase or penicillin-V amidase to activate prodrugs specifically at site of antibody targeting, for therapeutic treatment of solid tumors.

Drug-carrier conjugates have been used in the prior art to provide time-release drug delivery agents.

Couveur and Puisieux, 1993, *Adv. Drug Deliv. Rev.* 10: 141–162 provide a review of microcapsule (vesicular), microsphere (dispersed matrix) and microparticle (1–250 μm)-based drug delivery systems, based on degradation of particle with drug release, to provide time release of drugs, oral delivery via transit through the intestinal mucosa and delivery to Kupffer cells of liver.

Duncan, 1992, *Anticancer Drugs* 3: 175–210 provide a review of improved pharmacokinetic profile of in vivo drug release of anticancer drugs using drug-polymer conjugates.

Heinrich et al., 1991, *J. Pharm. Pharmacol.* 43: 762–765 disclose poly-lactide-glycolide polymers for slow release of gonadotropin releasing hormone agonists as injectable implants.

Wada et al. 1991, *J. Pharm. Pharmacol.* 43: 605–608 disclose sustained-release drug conjugates with lactic acid oligomers.

Specifically, polymer-conjugated drugs have been reported in the prior art, and attempts to adapt particulate conjugates have also been reported.

Ryser et al., U.S. Pat. No. 4,847,240, issued Jul. 11, 1989, provides cationic polymers for conjugation to compounds that are poorly transported into cells. Examples include the antineoplastic drug methotrexate conjugated with polylysine and other polycationic amino acids as carriers.

Ellestad et al., U.S. Pat. No. 5,053,394, issued Oct. 1, 1991, provides carrier-drug conjugates of methyltrithiol antibacterial and antitumor agents with a spacer linked to a targeting molecule that is an antibody or fragment thereof, growth factors or steroids.

Kopecek et al., U.S. Pat. No. 5,258,453, issued Nov. 2, 1993, provides antitumor compositions comprising both an anticancer drug and a photoactivatable drug attached to a copolymeric carrier by functional groups labile in cellular lysosomes, optionally containing a targeting moiety that are monoclonal antibodies, hormones, etc.

Yatvin et al., U.S. Pat. No. 5,543,390, issued Aug. 6, 1996, discloses microparticles conjugated to antiproliferative drugs.

Yatvin et al., U.S. Pat. No. 5,543,391, issued Aug. 6, 1996, discloses microparticles conjugated to antiproliferative drugs.

Negre et al., 1992, *Antimicrob. Agents and Chemother.* 36: 2228–2232 disclose the use of neutral mannose-substituted polylysine conjugates with an anti-leischmanial drug (allopurinol riboside) to treat murine infected macrophages in vitro.

Yatvin, 1991, *Select. Cancer. Therapeut.* 7: 23–28 discusses the use of particulate carriers for drug targeting.

Hunter et al., 1988, *J. Pharm. Pharmacol.* 40: 161–165 disclose liposome-mediated delivery of anti-leischmanial drugs to infected murine macrophages in vitro.

Saffran et al., 1986, *Science* 233: 1081–1084 disclose drug release from a particulate carrier in the gut resulting from degradation of the carrier by enzymes produced by intestinal microflora.

A particular human disease related to infection of phagocytic cells by a microorganism is tuberculosis, caused by infection with *Mycobacterium tuberculosis*. This disease typically arises after inhalation in phagocytic macrophages in the lung, where characteristic localized sites of infection (termed tubercules) are formed and comprise sites of further systemic infection. Although previously well-controlled by antibiotics such as isoniazid, the development of drug-resistance by the infectious agent, and the increased numbers of immune-compromised individuals with the outbreak of the AIDS crisis has created a near epidemic of tuberculosis cases world-wide. In 1997, the World Health Organization reported tuberculosis to be the world's top infectious killer.

About one-third of new tuberculosis cases are resistant to the current drug-treatment regimes. It is estimated that drug-resistant tuberculosis accounts for between 2% and 14% of total tuberculosis cases worldwide. As tuberculosis is spread by air-borne droplets from coughing by infected individuals, and its spread is further facilitated in crowded environments such as cities, there is a great potential for a precipitous increase in tuberculosis infections that will not be easily controlled by conventional medicinal intervention such as isoniazid administration. Lethal strains of tuberculosis have the potential for rapid spread, since only about one in ten patients receives the medical treatment necessary to contain and successfully treat the disease. Thus, there exists in this art a need to develop new and better treatments for tuberculosis, particularly tuberculosis infections resistant to traditional antibiotic treatments.

SUMMARY OF THE INVENTION

The present invention is directed to improved reagents and methods for delivering antibiotic, antimicrobial or antiviral compounds, drugs or agents to phagocytic cells in vivo and in vitro. In particular, the invention is directed towards delivery of antimicrobial compounds, drugs and agents specific for treatment of tuberculosis and other Mycobacterium-caused diseases in humans.

The invention provides drug delivery vehicles that are microparticles conjugated to, coated with, or impregnated with one or a multiplicity of antimicrobial compounds, drugs or agents specific for the treatment of tuberculosis and other Mycobacterium-caused diseases in animals, most preferably humans. In one preferred embodiment, the antibiotic, antimicrobial or antiviral compound, drug or agent is a prodrug of an activated form of the anti-tuberculosis drug isoniazid. In a second preferred embodiment, the antibiotic, antimicrobial or antiviral compound, drug or agent is a competitive inhibitor of long chain enol-acyl carrier protein reductase (termed InhA), an $M.$ $tuberculosis$-encoded enzyme required for production of an essential bacterial cell wall component, mycolic acid. In a third preferred embodiment, the antibiotic, antimicrobial or antiviral compound, drug or agent is an irreversible inhibitor of InhA, otherwise termed a "suicide substrate" herein.

In one aspect, this delivery system achieves specific delivery of antibiotic, antimicrobial or antiviral compounds, drugs or agents to phagocytic cells through conjugating the antibiotic, antimicrobial or antiviral compound, drug or agent with a particular microparticle via a cleavable linker moiety that is specifically cleaved in an infected cell. Alternatively, specific delivery is achieved by impregnating the antibiotic, antimicrobial or antiviral compound, drug or agent into a porous microparticle, which is then coated with a specifically-degraded coating material that is specifically degraded in an infected cell. In yet another alternative embodiment, the delivery system comprises a nonporous microparticle wherein an antibiotic, antiviral and antimicrobial compound, drug or agent is prepared as a coating on the particle surface, and the particle is then further coated by a specifically-degradable coating material that is specifically degraded in an infected cell. In another embodiment, a porous or non-porous microparticle is impregnated or coated with a first antibiotic, antimicrobial or antiviral compound, drug or agent, then coated with a specifically-degradable or non-specifically degradable coating material, then further coated with a second coating of a antibiotic, antimicrobial or antiviral compound, drug or agent that can be the same or different than the first coating of antibiotic, antimicrobial or antiviral compound, drug or agent, then further coated with a second coating of a specifically-degradable or non-specifically degradable coating material that may be the same or different than the first specifically-degradable or non-specifically degradable coating, wherein the microparticle can comprise a multiplicity of such alternating coatings of antibiotic, antimicrobial or antiviral compounds, drugs and agents and specifically-degradable or non-specifically degradable coatings, provided that the final coating of the microparticle is a specifically-degradable coating that is specifically degraded only in a cell infected with a pathological or disease-causing microorganism, most preferably a Mycobacterium species. In each embodiment of the microparticles of the invention, specific release of the antibiotic, antimicrobial or antiviral compounds, drugs and agents from the microparticle is achieved by enzymatic or chemical release of the compound, drug or agent from the microparticle by cleavage of the cleavable linker moiety or the specifically-degradable coating material in infected phagocytic cells. Such microparticles can be produced to provide sequential, delayed, sustained or controlled release of the antibiotic, antimicrobial or antiviral compounds, drugs or agents of the invention.

In a first aspect, the specific delivery of antibiotic, antimicrobial or antiviral compounds, drugs or agents achieved by the present invention results from conjugating, impregnating or coating such compounds, drugs or agents to microparticles. Specific intracellular accumulation and facilitated cell entry is mediated by the phagocytic uptake of microparticle-conjugated antibiotic, antimicrobial or antiviral compounds, drugs or agents by such cells. Preferred embodiments of phagocytic cellular targets include phagocytic hematopoietic cells, preferably macrophages and phagocytic neutrophiles, most preferably macrophages, mononuclear cells and phagocytic neutrophiles from lung tissue.

Particularly preferred targets of the microparticle-conjugated antibiotic, antimicrobial or antiviral compounds, drugs or agents of the invention are phagocytic cells, including phagocytic hematopoietic cells, preferably macrophages and phagocytic neutrophiles and most preferably macrophages, mononuclear cells and phagocytic neutrophiles from lung tissue that are infected with $M.$ $tuberculosis, M. africanum, M. bovis$ or any other microorganism that causes tuberculosis in an animal, most preferably a human. Also preferred targets are cells infected with $M. leprae, M. avium, M. intracellulare, M. scrofulaceum, M. kansasii, M. xenopi, M. marinum, M. ulcerans, M. fortuitum$ and $M. chelonae$. For such cells, the embodiments of the microparticle-conjugated antibiotic, antimicrobial or antiviral compounds, drugs or agents of the invention are comprised of cleavable linker moieties or specifically-degradable coatings whereby chemical or enzymatic cleavage of said linker moieties or coatings is specific for tuberculosis- or other disease-causing Mycobacterium-infected phagocytic cells. Such microparticles provide for infected cell-specific release of antibiotic, antimicrobial or antiviral compounds, drugs or agents, such as isoniazid, activated isoniazid, rifampin, streptomycin, ethambutol and pyrazinamide, and competitive, non-competitive and "suicide substrate" InhA inhibitors or any other anti-tuberculosis or anti-Mycobacterium drug or agent, in such infected cells. It is understood that all phagocytic cells are expected to take up such microparticle-conjugated or coated antibiotic, antimicrobial or antiviral embodiments of the invention. However, it is an advantageous feature of the microparticle-conjugated antibiotic, antimicrobial or antiviral compounds of the invention that specific release of biologically-active forms of such antibiotic, antimicrobial or antiviral drugs or agents is dependent on the presence of the infectious microorganism in the phagocytic cell.

The invention provides compositions of matter and pharmaceutical compositions thereof comprising a porous microparticle into which is impregnated with an antibiotic, antimicrobial or antiviral compound, the impregnated porous microparticle being further coated with a specifically-degradable coating material. In this aspect of the invention, the specifically-degradable coating material is specifically degraded inside a phagocytic mammalian cell infected with a tuberculosis-causing or other Mycobacterium-associated disease-causing microorganism, allowing the specific release of the antibiotic, antimicrobial or antiviral compound within the infected cell. In preferred embodiments, the specifically-degradable coating material is a substrate for a protein having an enzymatic activity found specifically in phagocytic cells infected with a tuberculosis-causing or other Mycobacterium-associated disease-causing microorganism. In additional preferred embodiments, the specifically-degraded coating material is chemically cleaved under physiological conditions that are specific for phagocytic cells infected with a tuberculosis-causing microorganism. In preferred embodiments, the antibiotic, antimicrobial or antiviral compound, drug or agent impregnating the microparticle is an activated embodiment of said compound, drug or agent, as defined herein. In alternative embodiments, the microparticle is impregnated with a multiplicity of antibiotic, antimicrobial or antiviral compounds, drugs or agents.

In alternative aspects, the coating material is nonspecifically cleaved chemically or enzymatically inside a phagocytic cell, wherein the antibiotic, antimicrobial or antiviral compound, drug or agent is in a form that is only specifically activated in the cell when the cell is infected with a tuberculosis-causing or other Mycobacterium-associated disease-causing microorganism (wherein said antibiotic, antimicrobial or antiviral compounds, drugs or agents are termed "prodrugs" as defined herein when provided in this form). In alternative embodiments, the microparticle is impregnated with a multiplicity of antibiotic, antimicrobial or antiviral compounds, drugs or agents or prodrug embodiments thereof. In preferred embodiments of the invention, the antibiotic compound is a specifically bactericidal or bacteriostatic against a microorganism that causes tuberculosis in an animal, most preferably a human, most preferably M. tuberculosis, M. africanum, M. bovis. Preferred antibiotic compounds used to impregnate such porous microparticles include activated isoniazid, rifampin, streptomycin, ethambutol and pyrazinamide, and competitive, uncompetitive, non-competitive and "suicide substrate" InhA inhibitors or any other anti-tuberculosis or anti-Mycobacterium compound, drug or agent. Activated and prodrug embodiments of these or other antibiotic, antimicrobial or antiviral compounds, drugs or agents are also preferred, and activated embodiments of said drugs are particularly preferred.

In preferred embodiments, the antimycobacterial drugs used in the practice of the invention are "activated" embodiments (as defined herein) of competitive, uncompetitive, non-competitive and "suicide substrate" inhibitors of long chain enol-acyl carrier protein reductase (InhA), a Mycobacterium-specific enzyme necessary for the production of mycolic acid, which an essential component of the mycobacterial cell wall. Inhibition of this enzyme by isoniazid is the basis of current anti-tuberculosis treatment modalities, and resistance to isoniazid is the principle form of drug resistance exhibited by mycobacteria. The compounds of the invention overcome resistance by being "pre-activated", i.e., these compounds do not rely on activation in the mycobacterium-infected cell for activity (unlike compounds do not rely on activation in the mycobacterium-infected cell for activity (unlike isoniazid itself). Thus, it is expected that resistance is less likely to be developed against these drugs. In a preferred embodiment, these compounds have the generic structure:

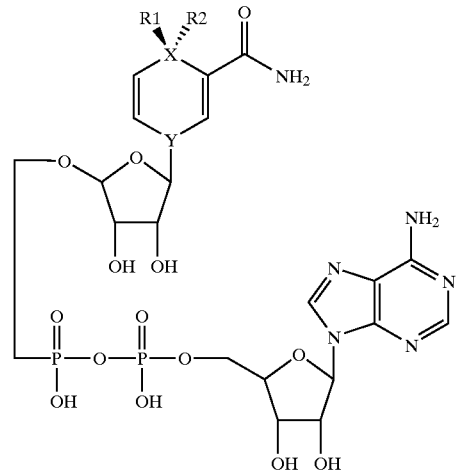

wherein X can be C or O; Y can be N or C; R1 and R2 can each be independently an electron pair, H, $CH_3$, $CH_2$–$CH_3$, or $O(CH_2)_3O$ or together can be $=O$, $=CH_2$, —$CH_2$—$CH_2$—, $=CH$—$CH=_2$, $=CH$—$COOCH_2$—$CH_3$, or $OCH_2$.

The invention also provides compositions of matter and pharmaceutical compositions thereof comprising a nonporous microparticle onto which is coated an antibiotic, antimicrobial or antiviral compound, the coated nonporous microparticle being further coated with a specifically-degradable coating material. In this aspect of the invention, the specifically-degradable coating material is specifically degraded inside a phagocytic mammalian cell infected with a tuberculosis-causing or other Mycobacterium-associated disease-causing microorganism, allowing the specific release of the antibiotic, antimicrobial or antiviral compound within the infected cell. In preferred embodiments, the specifically-degradable coating material is a substrate for a protein having an enzymatic activity found specifically in phagocytic cells infected with a tuberculosis-causing or other Mycobacterium-associated disease-causing microorganism. In additional preferred embodiments, the specifically-degraded coating material is chemically cleaved under physiological conditions that are specific for phagocytic cells infected with a tuberculosis-causing microorganism. In preferred embodiments, the antibiotic, antimicrobial or antiviral compound, drug or agent coating the microparticle is an activated embodiment of said compound, drug or agent, as defined herein. In alternative aspects, the coating material is nonspecifically cleaved chemically or enzymatically inside a phagocytic cell, wherein the antibiotic, antimicrobial or antiviral compound, drug or agent is in a form that is only specifically activated in the cell when the cell is infected with a tuberculosis-causing or other Mycobacterium-associated disease-causing microorganism (wherein said antibiotic, antimicrobial or antiviral compound, drug or agent is termed a "prodrug" as defined herein when provided in this form). In alternative embodiments, the microparticle is coated with a multiplicity of antibiotic, antimicrobial or antiviral compounds, drugs or agents or prodrug embodiments thereof.

In preferred embodiments of the invention, the antibiotic compound is a specifically bactericidal or bacteriostatic against a microorganism that causes tuberculosis in an animal, most preferably a human, most preferably M.

*tuberculosis, M africanum, M bovis.* Preferred antibiotic compounds used to coat such porous microparticles include activated isoniazid, rifampin, streptomycin, ethambutol and pyrazinamide, and competitive, uncompetitive, non-competitive and "suicide substrate" InhA inhibitors or any other anti-tuberculosis or anti-Mycobacterium compound, drug or agent. Activated and prodrug embodiments of these or other antibiotic, antimicrobial or antiviral compounds, drugs or agents are also preferred, and activated embodiments are particularly preferred. Most preferred embodiments have the generic structure disclosed above Additional embodiments of the compositions of matter and pharmaceutical compositions thereof comprising the porous and non-porous, impregnated or coated microparticles of the invention are provided wherein the porous or non-porous microparticle is impregnated or coated with a first antibiotic, antimicrobial or antiviral compound, drug or agent, then coated with a specifically-degradable or non-specifically degradable coating material, then further coated with a second coating of a antibiotic, antimicrobial or antiviral compound, drug or agent that can be the same or different than the first coating of antibiotic, antimicrobial or antiviral compound, drug or agent, then further coated with a second coating of a specifically-degradable or non-specifically degradable coating material that may be the same or different than the first specifically-degradable or non-specifically degradable coating, wherein the microparticle can comprise a multiplicity of such alternating coatings of antibiotic, antimicrobial or antiviral compounds, drugs or agents and specifically-degradable or non-specifically degradable coatings, provided that the final coating of the microparticle is a specifically-degradable coating that is specifically degraded in a cell infected with a pathological or disease-causing microorganism, most preferably a Mycobacterium species. Such microparticles can be produced to provide sequential, delayed, sustained or controlled release of the antibiotic, antimicrobial or antiviral compounds, drugs or agents of the invention. In each embodiment of the microparticles of the invention, specific release of the antibiotic, antimicrobial or antiviral compound, drug or agent from the microparticle is achieved by enzymatic or chemical release of the compound, drug or agent from the microparticle by cleavage of the specifically-degradable coating material in infected phagocytic cells. Antibiotic, antimicrobial and antiviral compounds, drugs or agents released by non-specific chemical or enzymatic degradation are advantageously provided in inactive, prodrug forms that are specifically activated in cells infected with pathological or disease-causing microorganism, most preferably a Mycobacterium species. In one alternative embodiment of this aspect of the invention, the "gatekeeper" for release of the antibiotic, antimicrobial or antiviral drug, compound or agent coating the microparticle is the ultimate, specifically-degraded coating material, which is only removed from the microparticle in a phagocytic cell infected with a pathological or disease-causing microorganism, most preferably a Mycobacterium species. In preferred embodiments, the antibiotic, antimicrobial or antiviral agent is provided in an activated form as defined herein. In said preferred embodiments, the "gatekeeper" specifically-degraded coating material prevents release of physiologically-significant amounts of the activated compound, drug or agent anywhere other than inside an infected phagocytic cell, most preferably a phagocytic cell infected with a pathological or disease-causing microorganism, most preferably a Mycobacterium species.

In an alternative embodiment, each antimicrobial, antibiotic or antiviral drug, compound or agent is provided in the form of a prodrug that is activated only in a phagocytic cell infected with said pathological or disease-causing microorganism, most preferably a Mycobacterium species. In this alternative embodiment, delivery of the antibacterial, antibiotic or antiviral drug, compound or agent in an active form to a phagocytic cell will only occur in such a cell that is infected with a pathological or disease-causing microorganism, most preferably a Mycobacterium species wherein both the specifically-degradable coating and the prodrug are degraded and activated, respectively, by an enzymatic or chemical reaction specific for the infected cell.

In these aspects of the invention, the antibiotic, antimicrobial or antiviral compound, drug or agent will be understood to dissolve from the surface of the microparticle upon enzymatic or chemical degradation of the organic coating material. Release of the antibiotic, antimicrobial or antiviral compound, drug or agent can be accomplished simply be mass action, i.e., whereby the compound dissolves from the surface of the nonporous microparticle into the surrounding cytoplasm within the cell, or leaches or is released from the porous microparticle.

The invention also provides compositions of matter and pharmaceutical compositions thereof comprising an antibiotic, antimicrobial or antiviral compound, drug or agent linked to a microparticle via a cleavable linker moiety. The cleavable linker moieties of the invention comprise two linker functional groups, wherein the cleavable linker moiety has a first end and a second end. The microparticle is attached to the first end of the cleavable linker moiety through a first linker functional group and the antibiotic, antimicrobial or antiviral compound, drug or agent is attached to the second end of the cleavable linker moiety through a second linker functional group. The cleavable linker moieties of the invention are specifically cleaved inside an infected phagocytic mammalian cell, for example, a phagocytic cell infected with a tuberculosis-causing or other Mycobacterium-associated disease-causing microorganism. In preferred embodiments, the cleavable linker moieties of the invention comprise a substrate for a protein having an enzymatic activity found specifically in phagocytic cells infected with a tuberculosis-causing or other Mycobacterium-associated disease-causing microorganism. In a particular embodiment of this aspect of the invention, the cleavable linker moiety is a peptide of formula (amino acid)$_n$, wherein n is an integer between 2 and 100, preferably wherein the peptide comprises a polymer of one or more amino acids. In additional preferred embodiments, the cleavable linker moieties of the invention are moieties that are chemically cleaved under physiological conditions that are specific for phagocytic cells infected with a tuberculosis-causing microorganism. In preferred embodiments, the antibiotic, antimicrobial or antiviral compound, drug or agent impregnating the microparticle is an activated embodiment of said compound, drug or agent, as defined herein. In alternative embodiments, the microparticles of the invention are provided comprising either a multiplicity of antimicrobial, antibiotic or antiviral compounds, drugs, or agents or a multiplicity of cleavable linker moieties, or both.

In alternative aspects, the cleavable linker moieties are nonspecifically cleaved chemically or enzymatically inside a phagocytic cell, wherein the antibiotic, antimicrobial or antiviral compound, drug or agent is in a form that is only specifically activated in the cell when the cell is infected with a tuberculosis-causing or other Mycobacterium-associated disease-causing microorganism (wherein said antibiotic, antimicrobial or antiviral compounds, drugs or agents are termed "prodrugs" as defined herein when provided in this form).

In preferred embodiments of the invention, the antibiotic compound is a specifically bactericidal or bacteriostatic against a microorganism that causes tuberculosis in an animal, most preferably a human, most preferably *M. tuberculosis, M. africanum, M. bovis*. In preferred embodiments, the antibiotic compound is isoniazid, activated isoniazid, rifampin, streptomycin, ethambutol and pyrazinamide, and competitive, uncompetitive, noncompetitive and "suicide substrate" InhA inhibitors or any other anti-tuberculosis or anti-Mycobacterium compound, drug or agent. Activated and prodrug embodiments of these or other antibiotic, antimicrobial or antiviral compounds, drugs or agents are also preferred.

The most preferred embodiments of the microparticles of the invention comprise prodrugs forms of activated isoniazid conjugates with NAD (termed isoniazid-NAD analogues, of INA, herein) that are inactivated by covalent modification of the activated drug to block binding of the drug to NAD-requiring enzymes, including InhA and mammalian cell, most preferably human cell-derived, NAD requiring enzymes. In the most preferred embodiments of this aspect of the invention, the inactivated prodrug form is specifically activated only in Mycobacterium-infected cells. In one aspect, such specific cleavage is due to a chemical linkage in the derivative that is labile within the infected cell due to conditions caused by or that result from infection of the cell with the mycobacteria. In another preferred aspect, such specific cleavage is due to an enzymatic activity which is produced either by the mycobacteria itself or by the cell as the result of infection with said mycobacteria, wherein the linkage is enzymatically cleaved by the enzymatic activity. In particularly preferred embodiments, the derivatizing group is a urea moiety that is specifically cleaved in Mycobacteria-infected cells by a mycobacteria-encoded urease.

The microparticle-drug conjugates of this invention have numerous advantages. First, the drug-microparticle conjugates are specifically taken up by phagocytic mammalian cells. Second, antibiotic, antimicrobial or antiviral compound, drugs or agents, most preferably anti-tuberculosis and anti-Mycobacterium compounds, drugs or agents comprising the drug-microparticle conjugates of the invention, are linked to the microparticle or covered by a coating comprising a specifically degradable moiety or material that is specifically cleaved upon entry into appropriate phagocytic cells, i.e., phagocytic cells infected with a tuberculosis-causing or other Mycobacterium-associated disease-causing microorganism. Third, the conjugates of the invention can be combined with other drug delivery approaches to further increase specificity and to take advantage of useful advances in the art. Fourth, the specificity of microparticle delivery to phagocytic cells and the specificity of conjugated antibiotic, antimicrobial or antiviral compound, drug or agent release in infected phagocytic cells permits the use and administration of efficacious antibiotic, antimicrobial or antiviral compounds, drugs or agents that are otherwise too toxic to be administered directly to an animal. Fifth, the specific delivery of the microparticles of the invention to phagocytic cells, and the specific release of antibiotic, antimicrobial or antiviral compounds, drugs or agents, and particularly activated embodiments thereof, permits direct administration of forms of said compounds, drugs and agents as they are activated by infectious organism-specific enzymatic or chemical modification, thereby providing a way of overcoming common forms of resistance to otherwise or previously efficacious antibiotic, antimicrobial or antiviral compounds, drugs or agents.

Thus, the invention also provides a method of killing a microorganism infecting a mammalian cell, preferably a phagocytic mammalian cell. This method comprises contacting an infected phagocytic mammalian cell with the compositions of matter or pharmaceutical compositions of the invention in vivo or in vitro. The invention also provides methods for treating microbial infections in an animal, most preferably a human wherein the infecting microbe is present inside a phagocytic cell in the human, the method comprising administering a therapeutically effective amount of the compositions of matter or pharmaceutical compositions of the invention to the human in a pharmaceutically acceptable carrier. Thus, the invention also provides pharmaceutical compositions comprising the compositions of matter of the invention in a pharmaceutically acceptable carrier. In most preferred embodiments, the infecting microorganism is a tuberculosis-causing microorganism such as *M. tuberculosis, M. africanum* or *M. bovis.*

Thus, in a first aspect the invention provides compositions of matter, pharmaceutical compositions and methods for targeting antibiotic, antimicrobial or antiviral compounds, drugs and agents to phagocytic cells. In a second aspect, the invention provides compositions of matter, pharmaceutical compositions and methods for the specific release of antibiotic, antimicrobial or antiviral compounds, drugs and agents inside phagocytic cells. The invention in yet a third aspect provides compositions of matter, pharmaceutical compositions and methods for intracellular delivery of targeted antibiotic, antimicrobial or antiviral compounds, drugs and agents to phagocytic cells. In each of these aspects is provided compositions of matter, pharmaceutical compositions and methods for introducing antibiotic, antimicrobial or antiviral compounds, drugs and agents into phagocytic mammalian cells wherein the unconjugated compound, drug or agent would not otherwise enter said phagocytic cell, the compound, drug or agent would not be specifically targeted to said phagocytic cell or the compound, drug or agent would have deleterious or toxic effects on non-infected cells. In this aspect is included the introduction of said compounds, drugs or agents in antibiotic, antimicrobial or antiviral embodiments that would not otherwise enter the cell, for example, as charged embodiments or salts, or wherein the compound, drug or agent is unstable or has a short half-life. In addition, the antibiotic, antimicrobial or antiviral compounds, drugs and agents useful in this invention are provided in activated forms in which they are toxic to normal cells, or which are activated by infectious agent-specific enzymatic or chemical modifications, but which are conjugated to or coated within a microparticle of the invention and released only in phagocytic cells infected with a tuberculosis or other Mycobacterium-associated disease-causing microorganism. In yet another aspect is provided compositions of matter, pharmaceutical compositions and methods for the specific coordinated targeting of more than one antibiotic, antimicrobial or antiviral compound to infected phagocytic mammalian cells. In another aspect, the invention provides compositions of matter, pharmaceutical compositions and methods for the introduction and specific release of antibiotic, antimicrobial or antiviral compounds, drugs or agents, preferably anti-tuberculosis and anti-Mycobacterium compounds, drugs or agents, and other compounds into cells infected by a tuberculosis-causing or other Mycobacterium-associated disease-causing pathological microorganism. In a final aspect, the invention provides compositions of matter, pharmaceutical compositions and methods for sequential, delayed, sustained or controlled intracellular release of antibiotic, antimicrobial, or antiviral compounds, drugs or agents impregnated within a coated, porous microparticle, or coated onto a nonporous microparticle, wherein the degradation of either a layer of the coating or the microparticle or both provides said sequential, delayed, sustained or controlled intracellular release of the antibiotic, antimicrobial or antiviral compounds, drugs or agents of the invention.

Specific preferred embodiments of the present invention will become evident from the following more detailed description of certain preferred embodiments and the claims.

DETAILED DESCRIPTION OF THE PREFERRED EMBODIMENTS

Figure 1:
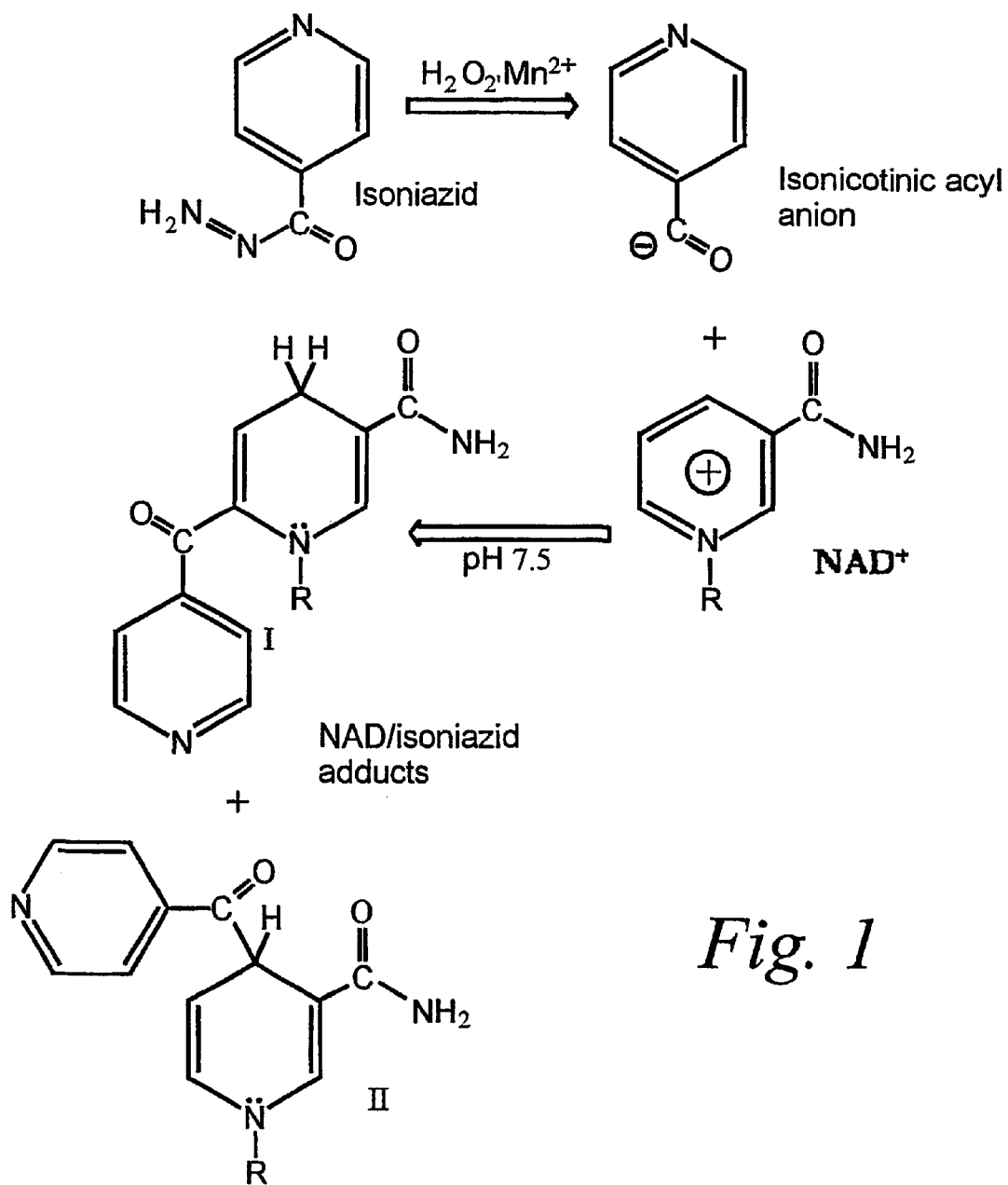
FIG. 1 is a diagram showing activation of the anti-tuberculosis drug isoniazid.

The present invention provides compositions of matter and methods for facilitating the entry of antibiotic, antimicrobial or antiviral compounds, drugs or agents into phagocytic cells. For the purposes of this invention, the term "antibiotic, antimicrobial or antiviral compounds, drugs or agents" is intended to encompass all naturally-occurring or synthetic chemical compounds capable of having a toxic, cytocidal or cytostatic effect on pathogenic or disease-causing microorganisms, most preferably tuberculosis-causing microorganisms including but not limited to *M. tuberculosis, M. africanum, M. bovis, M. leprae, M. avium, M. intracellulare, M. scrofulaceum, M. kansasii, M. xenopi, M. marinum, M. ulcerans, M. fortuitum* and *M. chelonae*. These compounds are intended to include but are not limited to all varieties of drugs or agents, particularly antibiotic and antimicrobial drugs, and most preferably anti-tuberculosis drugs and agents, including but not limited to isoniazid, activated isoniazid, rifampin, streptomycin, ethambutol, pyrazinamide, and competitive, uncompetitive, non-competitive and "suicide substrate" InhA inhibitors or any other anti-tuberculosis or anti-Mycobacterium compound, drug or agent.

In preferred embodiments, the antibiotic, antimicrobial or antiviral compound, drug or agent coating the microparticle is an activated embodiment of said compound, drug or agent, as defined herein, wherein said activated embodiment is not otherwise routinely administered to an animal because it is toxic to non-infected cells. The terms "activated" and "activated form" of antibiotic, antimicrobial or antiviral compounds, drugs or agents as provided herein are intended to encompass embodiments of said compounds, drugs or agents that are toxic to both infected and uninfected cells. These terms include embodiments wherein the compound, drug or agent is in a form, for example, that is the result of an infectious microbe-specific modification of the unactivated form of the compound, drug or agent. These terms also encompass compounds that have been enzymatically or chemically modified in an infected cell and have antibiotic, antimicrobial or antiviral properties conferred or enhanced thereby. In the latter instance, the terms in particular are related to embodiments whereby the pathological or disease-causing microorganism has developed resistance to the compounds, drugs or agents by attenuation, mutation or ablation of the chemical or enzymatic activity in the infected cell. Introducing the activated form of the compound, drug or agent directly into the infected phagocytic cell provides a route for overcoming these types of resistance. In this way, the invention provides a way of delivering the activated compound, drug or agent to the infectious microbe, even in the event that the microbe is resistant to the compound, drug or agent because it no longer efficiently effects said modification of the unactivated form of the compound drug or agent, whether by mutation, loss or attenuation of gene expression, selection or otherwise.

An illustration of this type of activation is shown in FIG. 1. In the Figure, the anti-tuberculosis drug isoniazid is gently oxidized in the presence of divalent manganese ion and hydrogen peroxide to provide the isonicotinic acyl anion. (This reaction is preferably performed in an aprotic solvent to stabilize the anion.) Under slightly basic conditions (pH 7.5) the anion reacts with the oxidized form of nicotinamide adenine dinucleotide (NAD+) to form isoniazid-NAD analogue, or INA as described herein, that inhibits long chain enol-acyl carrier protein reductase (InhA), an enzyme needed for synthesis of mycolic acid, a critical component of the *M. tuberculosis* cell wall. Inhibition of mycolic acid production is the molecular basis of isoniazid anti-tuberculosis activity.

In a second illustrative embodiment, an NAD analogue that inhibits InhA, most preferably INA, is derivatized by covalently linking a urea moiety at a position in the molecule involved in binding the molecule with NAD-requiring enzymes, including mammalian NAD-requiring enzymes and InhA. The activated isoniazid-NAD analogues of the invention are provided in a form that is inactive in a mammalian, most preferably a human, cell not infected with mycobacteria. In these embodiments, the analogue, most preferably INA, is derivatized at a conserved position in the NAD molecule involved in NAD binding to NAD-requiring enzymes. Most preferably, such positions include but are not limited to the formamide group of the pyridine portion of the NAD component of INA, and the 1-amino group of the adenine portion of the NAD component of INA. Derivatives containing blocking groups at these positions are severely inhibited (by at least about 10-fold in binding affinity) in binding to NAD-requiring enzymes.

Figure 2:
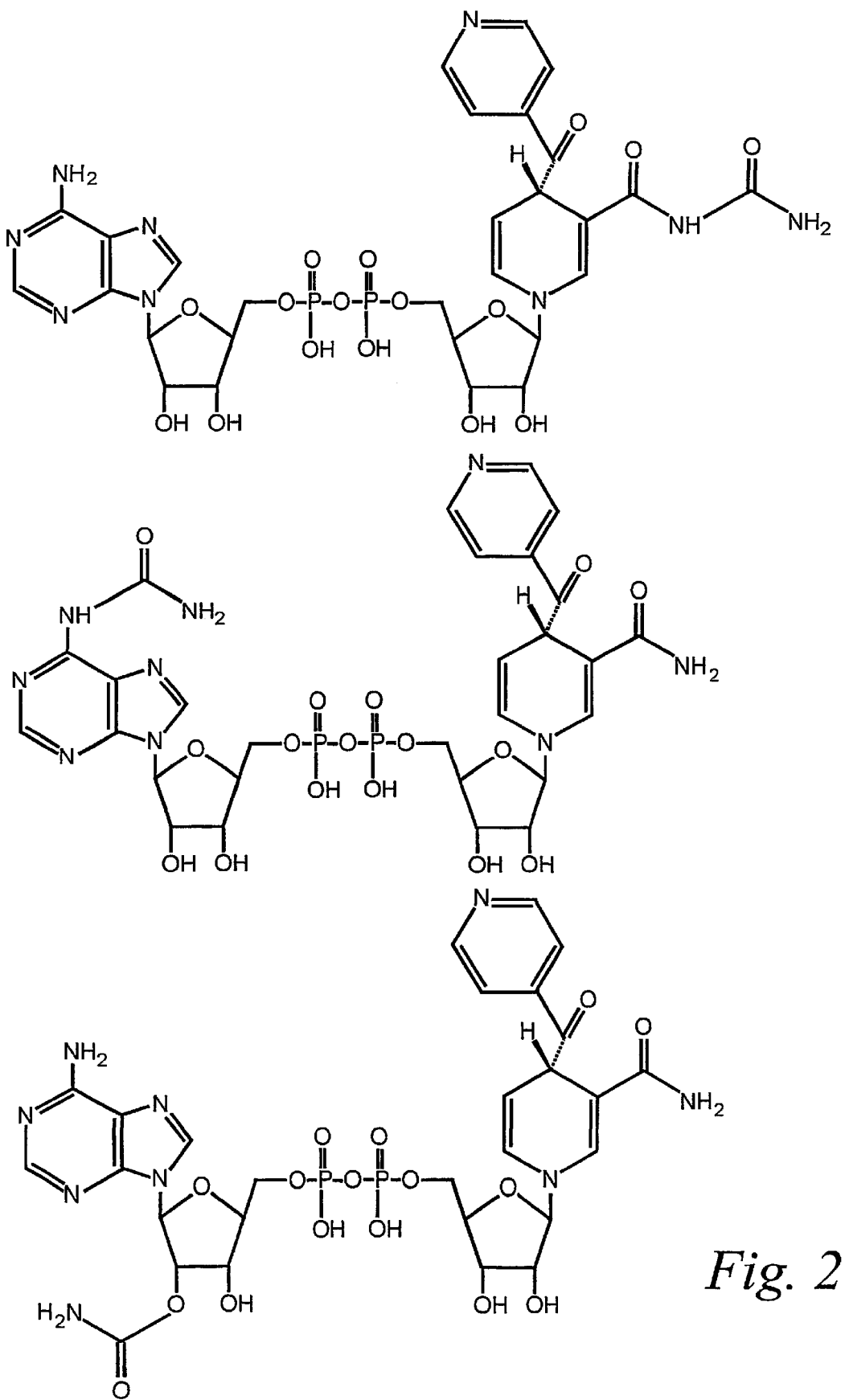
FIG. 2 is a schematic representation of the practice of the invention.

Delivery of these prodrugs to phagocytic cells is achieved using the microparticles of the invention. Specific activation of the derivatized prodrugs is achieved only in Mycobacteria-infected cells, because only those cells produce the conditions (chemical or enzymatic) under which the prodrug is turned into the active form of the drug. In preferred embodiments, the prodrug is a urea-derivatized form of INA, which is specifically activated to INA in Mycobactertium-infected cells by a specific urease made in those cells and not in any other mammalian, more preferably human, and most preferably phagocytic cells.

This invention provides microparticle-linked antibiotic, antimicrobial or antiviral compounds, drugs or agents wherein an antimicrobial drug, more preferably an anti-tuberculosis drug or anti-Mycobacterium drug is linked to a microparticle via a cleavable linker moiety, is impregnated within a porous microparticle or is coated onto a nonporous microparticle wherein said impregnated or coated microparticle is further coated with a specifically-degradable coating material. The microparticle-linked antibiotic, antimicrobial or antiviral compounds, drugs, or agents are taken up by phagocytic cells, most preferably hematopoietic phagocytic cells such as monocytes and macrophages, and the compounds, drugs and agents are specifically released in such phagocytic cells that are infected with a microorganism that produces (or whereby infection with the microorganism produces in the cell) an enzymatic or chemical activity that specifically cleaves the cleavable linker moiety or the specifically-degradable coating material. The practice of the invention is schematically represented in FIG. 2.

The term "anti-tuberculosis drug or anti-Mycobacterium drug" is intended to encompass any pharmacological agent effective in inhibiting, attenuating, combating or overcoming infection of phagocytic mammalian cells by a tuberculosis-causing or other disease-causing Mycobacterium species microbial pathogen in vivo or in vitro. Anti-tuberculosis drugs as provided by the invention include but are not limited to isoniazid, activated isoniazid, rifampin, capreomycin, ethionamide, cycloserine, ciprofloxacin, amikacin, streptomycin, ethambutol, pyrazinamide, and competitive, uncompetitive, non-competitive and "suicide substrate" InhA inhibitors as disclosed herein. Activated and prodrug embodiments of these or other antibiotic, antimicrobial or antiviral compounds, drugs or agents are also preferred. In preferred embodiments, the anti-mycobacterial drug is a drug that inhibits InhA, most preferably an activated form of isoniazid identified as isoniazid-NAD analogue and related compounds, that is provided as a prodrug as described herein. More preferably, the prodrug form of said InhA-inhibiting activated isoniazid derivatives is inactivated by covalent modification of the molecule at a site involved in binding to an NAD-requiring enzyme. Even more preferably, the modification is a modification that is specifically cleaved only in a mammalian cell, more preferably a human cell and most preferably a phagocytic cell that is infected with a Mycobacterium species. Most preferably, the covalent modification is attachment of a urea moiety to the formamide group of the nicotinamide portion of INA or to the 1-amino group of the adenine portion of INA, wherein said urea moiety is specifically cleaved in an infected cell by a urease produced by the infecting Mycobacterium species.

This invention provides microparticle-linked antibiotic, antimicrobial or antiviral compounds, drugs or agents for specific cell targeting to phagocytic mammalian cells. As used herein, the term "phagocytic mammalian cells" is intended to encompass but is not limited to monocytes, macrophages, peritoneal macrophages, alveolar macrophages, Kuppfer cells of the liver, macrophage cells resident in the central nervous system and the skin, all tissue inflammatory and noninflammatory macrophages, and phagocytic bone marrow cells, and most preferably alveolar macrophages.

In the antibiotic, antimicrobial and antiviral compounds, drugs or agents as provided by this invention, said antibiotic, antimicrobial or antiviral compounds, drugs or agents, most preferably anti-tuberculosis and anti-Mycobacterium compounds, drugs or agents, are linked to, impregnated into or coated onto microparticles that are specifically phagocytized by phagocytic mammalian cells. It is an advantage of the present invention that said antibiotic, antimicrobial and antiviral compounds, drugs or agents are specifically targeted to phagocytic mammalian cells, including, inter alia, monocytes and macrophages as described herein, via the microparticles that are a component of the antibiotic, antimicrobial and antiviral compounds, drugs or agents of the invention.

The term "microparticle" as used herein is intended to encompass any particulate bead, sphere, particle or carrier, whether biodegradable or nonbiodegradable, comprised of naturally-occurring or synthetic, organic or inorganic materials that is specifically phagocytized by phagocytic mammalian cells. In particular, the microparticle component of the antibiotic, antimicrobial or antiviral compounds, drugs or agents of the invention include any particulate bead, sphere, particle or carrier having a diameter of about 1 to about 5000 nanometers (about 0.001–5 $\mu$m), more preferably 1–5 $\mu$m in diameter. The microparticles of the invention are provided comprised of polystyrene, cellulose, silica, polyacrylamide, and various polysaccharides including dextran, agarose, cellulose and modified, crosslinked and derivatized embodiments thereof. Specific examples of the microparticles of the invention include polystyrene, cellulose, dextran crosslinked with epichlorohydrin (Sephadex™, Pharmacia, Uppsala, Sweden), polyacrylamide crosslinked with bisacrylamide (Biogel™, BioRad, USA), agar, glass beads and latex beads. Derivatized microparticles include microparticles derivatized with carboxyalkyl groups such as carboxymethyl, phosphoryl and substituted phosphoryl groups, sulfate, sulfhydryl and sulfonyl groups, and amino and substituted amino groups.

In one embodiment of the invention, said microparticle is a porous particle having a defined degree of porosity and comprised of pores having a defined size range, wherein the antibiotic, antimicrobial or antiviral compounds, drugs or agents are impregnated within the pores of the microparticle. In such embodiments, a chemically or enzymatically-degradable coating covers the surface or outside extent of the microparticle, wherein the coating is specifically chemically or enzymatically degraded within the particular infected phagocytic cell after phagocytosis and is not degraded systemically or in uninfected phagocytic cells. In preferred embodiments, the phagocytic cell is infected with a tuberculosis-causing or other Mycobacterium-associated disease-causing microorganism. In alternative embodiments, the porous microparticle is impregnated with a multiplicity of antibiotic, antimicrobial or antiviral compounds, drugs or agents.

In a second embodiment of the invention, the microparticle is either a porous or a nonporous particle. In such embodiments, the surface or outside extent of the microparticle comprises chemically functional groups that form covalent linkages with the antibiotic, antimicrobial or antiviral compounds, drugs or agents of the invention, preferably via a chemically or enzymatically cleavable linker moiety. In such embodiments, the cleavable linker moiety is specifically chemically or enzymatically cleaved within the particular infected phagocytic cell after phagocytosis and is not degraded systemically or in uninfected phagocytic cells. In preferred embodiments, the phagocytic cell is infected with a tuberculosis-causing or other Mycobacterium-associated disease-causing microorganism. In alternative embodiments, the microparticle is conjugated with a multiplicity of antibiotic, antimicrobial or antiviral compounds, drugs or agents, or comprises a multiplicity of cleavable linked moieties, or both.

In a third embodiment of the invention, the microparticle is nonporous and the antibiotic, antimicrobial or antiviral compound, drug or agent is coated on the outside of the microparticle. The microparticle is further coated with a specifically-degradable coating material to control the specific release of the antibiotic, antimicrobial or antiviral compounds, drugs or agents in infected phagocytic cells. In preferred embodiments, the phagocytic cell is infected with a tuberculosis-causing or other Mycobacterium-associated disease-causing microorganism. In such embodiments, a chemically or enzymatically-degradable coating covers the surface or outside extent of the microparticle, wherein the coating is specifically chemically or enzymatically degraded within the particular infected phagocytic cell after phagocytosis and is not degraded systemically or in uninfected phagocytic cells. In preferred embodiments, the phagocytic cell is infected with a tuberculosis-causing or other Mycobacterium-associated disease-causing microorganism. In preferred embodiments the antibiotic, antimicrobial or antiviral compound, drug or agent is an activated form of the compound, drug or agent, as defined herein. In alternative embodiments, the microparticle is coated with a multiplicity of antibiotic, antimicrobial or antiviral compounds, drugs or agents.

In alternative embodiments of this aspect of the invention, the coating material is a non-specifically degraded coating that is chemically or enzymatically degraded within any phagocytic cell, whether or not the cell is infected with a tuberculosis- or other Mycobacterium-associated disease-causing microorganism. In these embodiments, the antibiotic, antimicrobial or antiviral compound, drug or agent comprising said microparticles is provided as a "prodrug," defined herein as an inactive or non-toxic form of an antibiotic, antimicrobial or antiviral compound, drug or agent, whereby the prodrug is converted or activated in a phagocytic cell by a protein having an enzymatic activity found specifically in phagocytic cells infected with a tuberculosis-causing or other Mycobacterium-associated disease-causing microorganism. In preferred embodiments, the prodrug is an activated isoniazid derivative, such as INA, that is covalently modified at a position involved in binding of the derivative to an NAD-requiring enzyme such as InhA. In these embodiments, the covalent modification interferes with and inhibits binding by at least 10-fold, so that the prodrug derivative is essentially inactive against NAD-requiring enzymes without activation. Activation of the prodrug is achieved specifically in Mycobacterium-infected cells. In one aspect, such specific cleavage is due to a chemical linkage in the derivative that is labile within the infected cell due to conditions caused by or that result from infection of the cell with the mycobacteria. In another preferred aspect, such specific cleavage is due to an enzymatic activity which is produced either by the mycobacteria itself or by the cell as the result of infection with said mycobacteria, wherein the linkage is enzymatically cleaved by the enzymatic activity. In particularly preferred embodiments, the derivatizing group is a urea moiety that is specifically cleaved in Mycobacteria-infected cells by a mycobacteria-encoded urease. Alternatively, the prodrug of the antibiotic, antimicrobial or antiviral compound, drug or agent is specifically activated by chemical cleavage under physiological conditions that are specific for phagocytic cells infected with a tuberculosis-causing or other Mycobacterium-associated disease-causing microorganism.

In additional alternative embodiments, porous or non-porous microparticles are impregnated with or coated with a multiplicity of antibiotic, antimicrobial or antiviral compounds, drugs or agents. In certain embodiments of this aspect of the invention, the microparticles are impregnated with or coated with a multiplicity of antibiotic, antimicrobial or antiviral compounds, drugs or agents, and then coated with a specifically-degradable coating material as described herein. In other embodiments, the microparticles are impregnated with or coated with a multiplicity of antibiotic, antimicrobial or antiviral compounds, drugs or agents in prodrug (an inactive or non-toxic) form, and then coated with a nonspecifically-degradable coating material and specifically activated in phagocytic cells infected with a tuberculosis-causing or other Mycobacterium-associated disease-causing microorganism. In yet other embodiments, the microparticles are impregnated or coated with a first antibiotic, antimicrobial or antiviral compound, drug or agent, then coated with a specifically-degradable or nonspecifically-degradable coating material, and then further coated sequentially and in an alternating fashion with an antibiotic, antimicrobial or antiviral compound, drug or agent that can be the same or different than the first antibiotic, antimicrobial or antiviral compound, drug or agent, and further coated with a specifically-degradable or nonspecifically-degradable coating material, wherein is provided microparticles having a multiplicity of alternating layers of antibiotic, antimicrobial or antiviral compound, drug or agent and degradable coating materials. The final coating is most preferably a specifically-degraded material that is degraded only in infected phagocytic cells. In embodiments wherein any of the coating materials are nonspecifically degraded, the antibiotic, antimicrobial or antiviral compound, drug or agent uncoated thereby is provided in an inactive or nontoxic form that is specifically activated in a phagocytic cells infected with a tuberculosis-causing or other Mycobacterium-associated disease-causing microorganism. These embodiments of the microparticles of the invention permit the sequential, controlled, delayed or sustained release of antibiotic, antimicrobial or antiviral compounds, drugs or agents or multiplicity thereof in a phagocytic cell infected with a tuberculosis-causing or other Mycobacterium-associated disease-causing microorganism.

In all aspects of the invention, specific release or activation of the antibiotic, antimicrobial or antiviral compounds, drugs or agents is dependent on specific chemical or enzymatic cleavage of the coating or linker moieties inside cells infected with a tuberculosis-causing or other Mycobacterium-associated disease-causing microorganism after phagocytosis of the microparticle, or specific activation of a prodrug (inactive) form of said compound, drug or agent. The specificity of the cleavage of the linker or coating moieties as provided by this invention is the result of the combination of particular linker moieties or coating materials which are selected to be specifically cleaved inside the infected phagocytic cells. In one embodiment, such specific cleavage is due to a chemical linkage which is labile within the infected phagocytic cell due to conditions caused by or that result from infection of the phagocytic cell with the particular microbial pathogen. In another aspect, such specific cleavage is due to an enzymatic activity that is produced either by the microbial pathogen itself or by the phagocytic cell as the result of infection with said microbial pathogen, wherein the linkage is enzymatically cleaved by the enzymatic activity.

Examples of such combinations resulting in specific release of the antibiotic, antimicrobial or antiviral compound, drug or agent component of the compositions of matter and pharmaceutical compositions of the invention within infected phagocytic cells include but are not limited to a urea-based linker for use against a pathogen which produces urease (most preferably Mycobacteria spp.), as shown in FIG. 6.

In additional embodiments, the linker is a peptide comprising the amino acid sequence: -Ala-Xaa-Cys$_{Acm}$-Tyr-Cys-Arg-Ile-Pro-Ala-Cys$_{Acm}$-Ile-Ala-Gly-Asp-Arg-Arg-Tyr-Gly-Thr-Cys$_{Acm}$-Ile-Tyr-Gln-Gly-Arg-Leu-Trp-Ala-Phe-Cys$_{Acm}$-Cys$_{Acm}$-(SEQ. I.D. No.: 1), wherein the microbial pathogen expresses an enzymatic activity that specifically disables the endogenous antimicrobial peptide defensin (most preferably Mycobacterium spp.); nicotinic acid amides cleaved by nicotinamidases; pyrazinamides cleaved by pyrazinamidase; allolactose linkages cleaved by β-galactosidase; and allantoate linkages cleaved by allantoicase (most preferably Mycobacterium spp.); a peptide of formula (amino acid)$_n$, wherein n is an integer between 2 and 100, preferably wherein the peptide comprises a polymer of one or more amino acids and the microbial pathogen produces a protease or peptidase, more preferably wherein the peptide comprises a microbial-specific peptidase or protease cleavage site; and hydrolases that specifically cleave sugar and other saccharide moieties. Most preferably, an activated isoniazid analogue, such as INA, is derivatized with a urea moiety that is specifically cleaved in Mycobacteria-infected cells by a mycobacteria-encoded urease.

The antibiotic, antimicrobial or antiviral compounds, drugs or agents of this invention are useful in inhibiting, attenuating, arresting, combating and overcoming infection of phagocytic mammalian cells by pathogenic microorganisms in vivo and in vitro, particularly tuberculosis-causing species such as *M. tuberculosis, M. africanum* and *M. bovis*, as well as infection by *M. leprae, M. avium, M. intracellulare, M. scrofulaceum, M. kansasii, M. xenopi, M. marinum, M. ulcerans, M. fortuitum* and *M. chelonae*. To this end, the invention provides methods for treating an animal having a disease or disorder caused by one of these microorganisms, wherein the antibiotic, antimicrobial or antiviral compounds, drugs or agents of this invention are administered to an animal infected with a pathogenic microorganism that acutely or chronically infects phagocytic mammalian cells. In addition, prophylactic embodiments and uses of the pharmaceutical compounds of the invention are provided, for inoculating vulnerable phagocytic cells prior to or roughly coincident with infection with a pathological or disease-causing microorganism. The antibiotic, antimicrobial or antiviral compounds, drugs or agents of this invention for prophylactic or therapeutic uses are administered in a dosage and using a protocol sufficient to have an antimicrobial effect in the phagocytic cells of the animal. In addition, pharmaceutical compositions useful in the methods of the invention are also provided, comprising microparticles of the invention and a pharmaceutically-acceptable carrier, adjuvant or excipient. Routes of administration include oral, ocular, buccal, intranasal, intravenous, intramuscular, parenteral, transdermal, and rectal. In particularly preferred embodiments, the pharmaceutical compositions of the invention are provided as an aerosol or other easily-volatilized form, for delivery for example to the lung as provided by conventional inhalers and other pulmonary drug delivery devices and vehicles.

The following Examples illustrate certain aspects of the above-described method and advantageous results. The following examples are shown by way of illustration and not by way of limitation.

EXAMPLE 1

Development of Synthetic Procedures for Attaching Model Compounds to Microparticles via Urease-Cleavable Bonds In order to develop and assess efficient methods for conjugating antibiotic, antimicrobial and antiviral compounds, drugs and agents to microparticles, model systems are constructed using fluorescent-dye compounds as models for drugs. Using these model systems, procedures are developed for attaching fluorescent dyes to both soluble compounds and microparticles to form the soluble dye-linked conjugates and dye-linked microparticle conjugates, respectively.

A soluble dye-linked compound is synthesized comprising a dye and a cleavable carbamate group (shown in FIG. 3). The advantage of using a soluble dye-linked compound is that such conjugates can be rapidly synthesized and characterized using conventional synthetic-organic techniques (e.g., $^1H$ and $^{13}C$ NMR, mass spectroscopy, and HPLC analysis). After this soluble dye-linked compound is characterized, the rate of dye release via urease-catalyzed hydrolysis of the carbamate is measured. The soluble model dye-linked compounds are expected to act as substrates for urease based on the substrate specificities of closely-related urease substrates reported by Sandaram and Laidler (1970, *Canad. J. Biochem.* 48: 1132) and Fishbein and Carbone (1965, *J. Biol. Chem.* 240: 2407).

a. Synthesis of Soluble-Dye Linked Compounds

The soluble dye-linked compound synthesized herein is a mixed acetal of 3-phenyl propanal, as shown in FIG. 4. This compound is prepared by reacting 4-hydroxyl-7-nitro-2-1,3-benzoxadiazole (NBD, a fluorescent dye) and cyanic acid with 3-phenyl propanal using the following protocol. A nucleophilic addition of NBD by reaction of the NBD hydroxyl group with the aldehyde carbonyl of 3-phenyl propanal is performed using conventional techniques (Finley et al., 1980, *J. Org. Chem.* 45: 694; Jencks, 1969, Catalysis in Chemistry and Enzymology, McGraw Hill: N.Y., pp. 490–496) to form the hemiacetal. Production of the hemiacetal is favored by using anhydrous conditions in an aprotic solvent such as tetrahydrofuran and in a two-molar excess of the dye. The hemiacetal is then converted to the mixed acetal by cyanic acid according to the procedure of March (1985, Advanced Organic Chemistry: Reactions, Mechanisms and Structures, 3$^{rd}$ ed., J. Wiley & Sons, NY, pp. 791–792). Cyanic acid is formed by the dry distillation of cyanuric acid (Linard, 1938, *Anorg. Allgem. Chem.* 236: 200), and addition of cyanic acid to the hemiacetal results in formation of the mixed acetal of NBD and carbamate. The mixed acetal is stable in aqueous and organic solutions, and is purified by HPLC or by column chromatography.

b. Synthesis of Dye-Linked Microparticles

Dye-linked microparticles are prepared as follows. Biodegradable polyacryl-starch microparticles with an average diameter of 1–2 mm (Borissova et al., 1995, *J. Pharm. Sci.* 84: 256–262; Stjärnkvist et al., 1991, *J. Pharm. Sci.* 80: 436–440) are used because they are not immunogenic in mice (Artursson et al., 1986, *J. Pharm. Sci.* 75: 697–701), and no immunogenic response was detected using polyacryl-starch microparticles linked by lysine to dinitrophenol (Stjärnkvist et al., 1991, ibid.). These and other literature results indicate that neither the microparticle nor the combination of drug-linked microparticle should elicit an immunogenic response.

Polyacryl-starch microparticles are derivatized with a fluorescent dye (NBD) as follows. First, the starch molecules comprising the microparticle are derivatized with 4-aminobutyraldehyde diethyl acetal and carbonyl diimidazole (CDI) to yield microparticle-urethane linked butyraldehyde diethyl acetal (Stjärnkvist et al., 1991, ibid.). The derivatized microparticles are stirred in a solution of HCl in aqueous ethanol (pH 2) for 8 to 16 hr at room temperature, resulting in the hydrolysis of diethyl acetal to the aldehyde. The resulting microparticles have an accessible aldehyde moiety available for conjugation with the fluorescent dye. This aldehyde-derivatized microparticle is then further derivatized to form the mixed acetal of NBD and the carbamate as described above for synthesis of the soluble compounds.

The number of NBD dye molecules bound to the microparticle can be determined by taking a known weight of the microparticle dye-linked conjugate complex, hydrolyzing the carbamate bond with base, centrifuging the solution, and measuring the concentration of dye in the supernatant by HPLC. Based on the average microparticle size and density, the average number of dye molecules bound to each microparticle can be calculated.

c. Analytical Procedures

HPLC procedures for analysis and resolution of the fluorescent dye (NBD) and soluble dye-linked compounds are developed for analyzing cleaved fluorescent-dye compounds by urease enzymes.

In both cell-free and cell-dependent dye-release experiments, dye released from soluble compounds and from microparticle conjugates is monitored by an increase in the absorbance and/or fluorescence of the solution. In cell-free analyses, the concentration of dye released from the model compound and microparticle conjugates is measured after centrifugation of the insoluble material from the soluble non-particulate fluorescent dye, then measuring the concentration by HPLC. In cell-dependent cleavage experiments, cells are lysed with 0.1% Triton X-100 to release intact microparticles and cleaved fluorescent dye. The insoluble microparticle fraction is removed by centrifugation, and fluorescence of the cleared solution is measured to determine the concentration of free dye.

EXAMPLE 2

Measuring Release of Fluorescent Dye From Soluble Dye-Linked Compounds by Purified *Bacillus* Urease Dye release from soluble conjugates and dye-microparticle conjugates is measured by incubating the dye-conjugates in the presence of *Bacillus pasterurii* urease, obtained from Sigma Chemical Co. (St. Louis, Mo.). Urease activity is first assayed using standard procedures (Worthington Handbook, 1964, Worthington Biochemical Co., Freehold, N.J.). In this assay, urease activity is measured by coupling ammonia production from urea hydrolysis to glutamate dehydrogenase (GDH). A decrease in NADH concentration (measured spectrophotometrically) is proportional to the amount of glutamate formed from ammonia, which is produced by hydrolysis of urea by urease.

This same assay procedure is used to determine if *B. pasterurii* urease cleaves the carbamate linkage of the soluble dye-linked compounds. In this procedure, the mixed acetal produced as described in Example 1 is used as the urease substrate. Urease activity is measured spectrophotometrically using the GDH/NADH assay described above. Of particular interest is the rate of hydrolysis of the carbamate by urease.

Carbamate linker cleavage of fluorescent dye from conjugates microparticles is also assayed using *B. pasterurii* urease. In initial experiments, cell-free studies are performed with the dye-conjugated microparticles of the invention to determine time and concentration profiles (i.e., hydrolysis rates). In these experiments, known amounts of dye-linked microparticles are incubated with increasing amounts of purified urease at 37° C. to demonstrate the dependence of the cleavage reaction on enzyme concentration. In addition, the time course of the reaction is examined to confirm that cleavage products accumulate in a time-dependent fashion consistent with conventional enzyme-catalysis kinetics.

To determine if accumulation of hydrolyzed dye is the result of urease activity, control experiments are conducted under identical conditions and procedures except that urease enzyme is not added to the reaction mixture. In additional control experiments, the dye-conjugated microparticles of the invention are incubated with a macrophage extract not known to contain urease activity. In these experiments, a macrophage homogenate from macrophages from uninfected mice is prepared in a 3:1 dilution in 100 mM Hepes buffer, pH 7.5. The macrophage homogenate is first assayed for urease activity using the above-described conventional assay to confirm that the mouse macrophage homogenate does not contain urease activity.

These experiments are also useful for comparing dye release rates from the soluble dye conjugates and the microparticle dye conjugates.

EXAMPLE 3

Establishing Macrophage Cultures and Infecting Macrophages with *M. fortuitum* and *M. chelonei*

In order to assay the capacity of infected macrophages to specifically cleave carbamate linker-conjugated microparticles, in vitro macrophage cell cultures are developed and infected with the non-pathogenic mycobacteria strains *M. fortuitum* and *M. chelonei*, and then used to determine if the infected macrophages selectively release dye from the dye-linked microparticle conjugates complexes.

a. Mouse Macrophage Cell Cultures

Cell cultures are established from either (i) bone-marrow derived macrophages from C57/BL6 mice (H-2b), or (ii) transformed monocyte/macrophage isolated from C57/BL6 mice or BALB/c mice sources. 10–12 week old female mice, purchased from Bantin-Kingman (Seattle, Wash.) are used for these experiments. Mice are housed in plastic micro-isolater cages in a temperature- and humidity-controlled environment with a 12 hour light/dark cycle and fed Purina Lab Chow and water ad libitum. Cages, bedding, and food are autoclaved prior to use and all cage changes and mice handling are performed in laminar air-flow hoods. All mice are quarantined for a minimum of one week before experimental use.

b. Preparing the Cell Cultures Monolayers

Bone marrow derived macrophages (BMMF) from C57/BL6 mice (MHC haplotype H- $2^b$) and a monocyte/macrophage cell line (J774A.1; MHC haplotype H-$2^d$ ATCC, Manassas, Va.) are used for these studies. These cell types permit investigation of the efficacy of the dye-linked microparticles drug-delivery system in both primary cell culture isolates as well as transformed cell lines. In addition, inbred C57/B16 and BALB/c mice exhibit the Bcg$^s$ phenotype that is more permissive relative to infection with saprophytic and rapidly-growing mycobacteria such as *M. chelonei*, and *M. fortuitum* (Denis et al., 1990, *J. Leuk. Biol.* 47: 25–29; Radzioch et al., 1991, *J. Leuk. Biol.* 50: 263; van Furth, 1990, *Res. Microbiol.* 141: 256; Nibbering et al., 1994, *Scand. J. Immunol.* 40: 187).

BMMF cell cultures are established by collecting bone marrow cells from the long bones from the hind limbs of donor mice and culturing these cells in 24-well tissue culture plates at 5–10×10$^5$ cells/mL/well in DMEM culture medium supplemented with 10% FCS, 30% supernatant from L929 cells (a source GM-CSF-1; L cells are cultured in DMEM with 5% FCS) and antibiotics (100 U/mL penicillin and 100 mg/mL streptomycin sulfate). After 6–8 days at 37° C. and 6–7% $CO_2$, established BMMF monolayers are washed with DMEM and recultured in 10% FCS/DMEM without antibiotics for an additional 24 hours. Thereafter, BMMF monolayers are infected with viable M. fortuitum or M. chelonei as described below.

J774.1 cell cultures are plated in 24-well tissue culture plates using 2.5×10$^5$ cells/mL/well in 5% FCS/DMEM with antibiotics (penicillin and streptomycin). After 18–20 hours at 37° C. and 6–7% CO, J774.1 monolayers are washed three time with DMEM and recultured in fresh 5% FCS/DMEM without antibiotics, and immediately infected with viable M. fortuitum or M. chelonei as described below.

c. Infection of Cell Monolayers

BMMF and J774.1 cell monolayers are infected with viable M. fortuitum or M. chelonei. These mycobacterial species were chosen for these studies because (1) they exhibit more rapid in vitro intracellular growth than other mycobacteria (Denis et al., 1990, ibid.; Radzioch et al., 1991, ibid.; van Furth, 1990, ibid.; Nibbering et al., 1994, ibid.), (2) they are opportunistic pathogens for mammals (Steven et al., 1992, Cornea 11: 500; Sing et al., 1992, Tubercle & Lung Dis. 73: 305) and therefore represent appropriate models for more pathogenic mycobacteria, and (3) they both produce urease (Wayne and Kuica, 1986, Bergey's Manual of Systemic Bacteriology, Williams & Wilkins) and therefore present testable models for specific in vitro targeting of the inventive drug-delivery system.

M. fortuitum and M. chelonei are cultured in Middlebrook 7H9 liquid broth to midlog phase (3–4 days) and aliquots frozen at −80° C. Frozen aliquots are thawed and CFU titers determined by plating serial dilutions (in sterile PBS with 0.1% Tween 80) onto Middlebrook 7H 11 plates. The optimal multiplicity of infection (MOI) for the cell monolayers is determined in preliminary experiments, with mycobacteria added in 0.5 mL of 5–10% FCS/DMEM (without antibiotics). The optimal MOI is indicated by the maximal differential in mycobacterial CFU between 1 and 48 hours following infection, as this differential enhances the ability to detect urease activity.

Six hours following infection, cell monolayers are washed three times with warm DMEM (to remove extracellular bacteria) and recultured at 37° C. and 6–7% $CO_2$ in 5–10% FCS/DMEM without antibiotics, or with gentamicin sulfate to inhibit growth of extracellular mycobacteria. This in vitro infection methodology has been successfully demonstrated in preliminary experiments with slower growing mycobacteria. Although M. fortuitum and M. chelonei are rapidly growing mycobacterium, they still grow more slowly than most common bacteria. Therefore, a 24–28 hour period of infection for macrophage cell monolayers is required. Optimal in vitro infection of macrophages (of the Bcg$^s$ phenotype) with M. fortuitum or M. chelonei permits a 6-fold increase in intracellular mycobacteria at 24–48 hours following infection. Therefore, pulsing infected cell with microparticles at 12–18 hours after infection should provide sufficient numbers of infected macrophages as well as sufficient time for urease production by the intracellular mycobacteria, both of which represent essential elements in evaluating this unique, microparticle-based drug-delivery system.

EXAMPLE 4

Measuring Urease-catalyzed Release of Fluorescent Dye in Mycobacteria-infected Macrophage Cell Cultures The functional competence of M. fortuitum- and M. chelonei-infected macrophages to selectively release fluorescent dye from a dye-conjugated microparticle is determines as follows.

A. Incubation of Infected Macrophage Cultures with Fluorescent-Dye-Linked Microparticles Mouse bone-marrow derived macrophages or J774 cells are infected with M. fortuitum or M. chelonei as described above. Purified infected macrophage cells are incubated with dye-linked microparticles at a concentration of about 5–10 μM. Microparticle uptake is determined by lysing a known number of macrophage cells and determining the accumulated dye fluorescence in solution. The effect of microparticle uptake on functional competence of non-infected macrophages is determined by comparing the bactericidal capacity of microparticle-pulsed and non-pulsed phagocytic cell populations against subsequent infection with the intracellular bacterial pathogen Listeria monocytogenes (Peck, 1985, J. Immunol. Methods 82: 131–140; Drevets and Campbell, 1991, Infect. Immun. 59: 517–523; Drevets et al., 1992, J. Leuk. Biol. 52: 70–79; Barry et al., 1992, Infect. Immun. 60: 1625–1632)

B. Pulsing Infected Cells with Microparticles and Determination of Enzyme Activity At 12–18 hours following infection of cell monolayers, cells are incubated with a bolus of microparticles. The optimal size and number of microparticles used for cell uptake is determined as described in Example 3. At 2 hours after pulsing with the microparticles, cell monolayers are washed twice with warn DMEM and recultured at 37° C. and 6–7% $CO_2$ in 5–10% FCS/DMEM without antibiotics. At 6, 12, and 24 hours following addition of the microparticles, monolayer cells are lysed, either hypotonically with sterile water or with detergent (2.5% saponin or 0.1% NP-40; the quenching effects of detergents on fluorescence detection are evaluated prior to these studies). Cell supernatants from the lysed monolayers are clarified by centrifugation (10,000×g, 10 min) in microcentrifuge tubes equipped with 30 kilodalton molecular weight cut-off membranes. The relative fluorescence (as a measure of urease activity) of the supernatants from these centrifugations is determined by fluorescence spectrophotometry. Negative controls for these experiments consist of microparticle-pulsed, non-infected cell monolayers and infected, but non-pulsed cell monolayers. Positive controls for urease activity are commercially obtained enzyme preparations.

EXAMPLE 5

Preparing Activated Isoniazid Analogs

An activated isoniazid analog is prepared as described by Quemard et al. (1996, J. Am. Chem. Soc. 118: 1561–2). $^4$C-Isoniazid is incubated in the presence of H37R$_v$ enoyl-ACP reductase and katG-encoded catalase-peroxidase from wild type M. tuberculosis is incubated for 20 hours in a solution comprising 2 μM $MgCl_2$, 6% glycerol, 10 μM NADH, 100 μM isoniazid, 1.9 μM KatG and 9 μM NADH-specific enoyl-acyl carrier protein (ACP) reductase. After incubation, the reaction mixture is applied to a Pharmcia- PD-10 column, eluted and analyzed by liquid scintillation counting. Only in the presence of catalase-peroxidase are significant amounts of $^{14}$C-labeled isoniazid observed to co-elute with wild type enoyl-ACP reductase. The *M. tuberculosis* katG-encoded catalase-peroxidase enzyme produces radicals in the presence of isoniazid and hydrogen peroxide (Hillar & Loewen, 1995, *Arch. Biochem. Biophys.* 323: 438–446.) The fractions having radioactivity are combined and dialyzed against water using a dialysis membrane having a 10,000 daltons molecular weight cut-off. The aqueous solution containing $^{14}$C-labeled isoniazid-NADH complex is lyophilized and the resulting white powder collected and characterized.

Alternatively, the method of Magliozzo et al. (1996, *J. Am. Chem. Soc.* 118: 11303–4) is used to produce an isoniazid-NADH analog. In this method, isoniazid (20 mM) is incubated for 3 hr in 0.015 M phosphate buffer (pH 7.0) containing 10 mM NADH and 130 μM manganese (II) nitrate. The $Mn^{+2}$ cation has been reported to catalyze the aerobic decomposition of isoniazid in a radical-mediated mechanism (Ito et al., 1992, *Biochemistry* 31: 11606–11613). The isoniazid-NADH analog is isolated by HPLC chromatography using 50 mM ammonium acetate (pH 7) and a 0%–15% gradient of acetonitrile for elution. Fractions containing isoniazid-NADH analog are collected, concentrated and lyophilized to yield a powder.

EXAMPLE 6

Preparing Competitive and Irreversible Inhibitors of Long-chain Enol Acyl Carrier Protein Reductase Antimicrobial microparticles are produced comprising either competitive, non-competitive inhibitors or irreversible, "suicide substrate"-type inhibitors of long-chain enol acyl carrier protein reductase (InhA).

Competitive and irreversible inhibitors of ACP reductase are synthesized according to the methods and protocols disclosed in U.S. Pat. No. 6,329,060, incorporated by reference herein. Examples of these compounds are shown in FIG. 5.

EXAMPLE 7

Preparing Isoniazid-NAD Analogue Prodrugs

Activated anti-mycobacterial compounds as disclosed in Example 6 are modified to prodrugs that are specifically activated in Mycobacterium-infected cells as follows, using INA as a specific example of the method.

100 mg (0.10 mmol) of INA is dissolved in 10 mL of anhydrous pyridine, and 1.0 g (23.3 mmol) of cyanic acid (Linard, 1938; Merck Index, 1983) bubbled into the reaction mixture over 30 minutes, then stirred for 4 hr at 60° C. Excess pyridine is removed under high vacuum, then purified by HPLC, as described above. The resulting INA derivative has a urea functional group covalently linked to the 1-amino group of the adenine portion of the NAD component of INA (termed INA prodrug 1). This compound is characterized by $^1H$ NMR, $^{13}C$ NMR, and fast atom bombardment/mass spectrometry (FAB MS).

Alternatively, 100 mg (0.10 mmol) of INA is dissolved into 10 mL of anhydrous pyridine and cooled to 0° C. under nitrogen. Trimethylsilyl chloride (TMSCl; 5 g, 44.6 mmol) is added over 15 minutes, followed by stirring overnight at room temp. The excess TMSCl and pyridine are removed under high vacuum. Anhydrous tetrahydrofuran (THF; 20 mL) is added and the pyridine-HCl salt is removed by filtration. The THF fraction is cooled to −78° C., THF is added to keep the per TMS-INA in solution. N-Butyl lithium (1.0 mL of 0.10 M solution) is added dropwise followed by the addition of 1.0 g (23.3 mmol) of cyanic acid (Linard, 1938; Merck Index, 1983) that is bubbled into the reaction mixture over 30 minutes. The reaction is warmed and incubated at room temperature overnight. The derivatized product is isolated by the addition of 1.0 mL of water in 5 mL of ethanol, stirring at room temp for 3 hr, concentrating the reaction mixture and purifying the product by HPLC as described above. The resulting INA derivative has a urea functional group covalently linked to the nicotinamide formamide group (termed INA prodrug 2). This compound is characterized by $^1H$ NMR, $^{13}C$ NMR, and FAB MS.

EXAMPLE 8

Analysis of Isoniazid-NAD Analogue Prodrugs

Prodrug forms of activated anti-mycobacterial compounds as disclosed in Example 7 are tested to demonstrate Mycobacteria-specific activation of said prodrugs, using the urea-derivatized INA compounds of Example 3 as a specific example of the method.

Because the pyridine nucleotide binding site is highly conserved evolutionarily, it is expected that an inhibitor of a NAD-dependent bacterial enzyme is likely to inhibit mammalian (ADH) is assayed by the method of Zahlten (1980, *Biochem. Pharmacol.* 29: 1973–6) in the presence of the INA to determine a $K_i$ for the compound. To control for unexpected effects on the 340 nm absorbance by the analogs, these results are verified using a colorimetric assay according to Fibla and Gonzalez-Duarte (1993, *J. Biochem. Biophys Methods* 26: 87–93). An unrelated enzyme, NADH-dependent glutamate dehydrogenase is assayed according to the method of Meredith and Schmidt (1991, *Life Sci. Adv. Plant Physiol.* 10: 67–71) to confirm the ADH-derived results on the inhibitory potential of these analogs. The experiments described above will be repeated with urea-modified NAD analogs. These compounds should not have inhibitory activity, due to the alteration of portions of the compound that interact with the NAD binding site of the enzymes.

Implicit in the proposed mechanism of anti-tubercular activity of these prodrugs is that the mammalian cell, most preferably phagocytic cells such as macrophages, remains functional and intact long enough for the NAD analog prodrugs to kill the infecting mycobacterium. It is therefore essential to understand the degree of inhibition of NADPH-dependent enzymes as well, since these are the mainly biosynthetic enzymes required for macrophage repair. The NADPH-dependent enzymes isocitrate dehydrogenase (Dedhia et al., 1979, *Experimental Mycology* 3: 229–239) and malic enzyme (Mackall & Meredith, 1970, *Anal. Biochem.* 95: 270–4) are used to examine the effects of the INA derivatives on NADP-utilizing enzymes.

The ability of bacterial urease to produce active enzyme inhibitors is tested by in vitro incubation of the urea-modified NAD analogs with urease, both commercially obtained purified enzyme and partially purified bacterial urease obtained for these experiments. Urease release of inhibitors is evaluated in two ways. During incubation of the urea-modified analogs with urease under assay conditions, the release of the unmodified NAD analog is monitored by HPLC (Anderson & Anderson, 1983, *Anal. Biochem.* 134: 50–5), a method used successfully to quantitate a number of NAD analogs. Secondly, the ability to generate enzyme inhibition in the test systems (ADH, GDH) after incubation is tested and comprises the most compelling evidence that urease can activate the urea-derivatized NAD) analogues of the invention.

To demonstrate that urease cleaves the urea functional groups on INA prodrug 1 and INA prodrug 2 to yield INA, urease (urea amidohydrolase [EC 3.5.1.5]) from *M. tuberculosis* (Clemens et al., 1995, *J. Bacteriol.* 177: 5644–52), *M. fortuitum*, *M. chelonae*, and *Proteus vulgaris* are tested as follows.

Urease activity is measured by coupling with ammonia production, from urea hydrolysis, to a glutamate dehydrogenase (GDH) reaction (as described in the Worthington Handbook, 1994). The decrease in NADH concentration (measured spectrophotometrically at 340 nm) is proportional to the amount of glutamate formed from ammonia, which is produced by hydrolysis of urea. The concentration of the prodrug and INA are also monitored by HPLC.

The activated isonicotinic acid anion is recovered as a sodium or potassium salt and used to impregnate a porous microparticle that is then coated with a compound cleavable by a urease enzyme produced by a Mycobacterium species. This embodiment of the invention is prepared as follows.

Synthesis of Carbamate-derivatized Polymer Comprising the Microparticle Coating A carbamate-derivatized polymer used to coat a microparticle impregnated with a salt of an activated isonicotinic acid anion according to the invention is prepared as shown in FIG. 7. Commercially-available 2-deoxy-D-ribose (Sigma Chemical Co., St. Louis, Mo.) is converted to isopropylidene-protected Compound 2 using reaction conditions described by Renoll & Newman (1955, "D,L-Isopropylideneglycerol," Organic Synthesis Collective , Vol III, John Wiley & Sons, Inc.: N.Y., pp 502–4). A carbamate group is introduced using a procedure described by Kurzer (1963, "Arylures I. Cyanate Method," Organic Synthesis Collective, Vol. IV, John Wiley & Sons, Inc.: N.Y., pp. 49–51. The isopropylidene protecting group is removed under mild acidic conditions by adjusting the pH to pH 1.0 with dilute hydrochloric acid to yield Compound 3. Sodium periodate oxidation (as described by Schmid & Bryant, 1993, *Org. Syn.* 72: 6) of the vicinal diols of Compound 3 in aqueous solution yields the acyclic dialdehyde carbamate intermediate that is reduced with sodium cyanoborohydride under mild conditions (between pH 3 and 4) to yield Compound 4. Compound 4 is then converted to Compound 5 by the addition of 2.2 equivalents of commercially-available (Aldrich, Milwaukee, Wis.) allyl 2,2,2,-trichloroacetamidate and a catalytic amount of triflic acid at room temperature in a mixture (1:1 ratio) of dichloromethane and cyclohexane (as described in Wessel et al., 1985, *J. Chem. Soc. Perkin* 1: 2247–2250; Iversen & Bundle, 1981, *J. Chem. Soc. Chem. Comm.* 23: 1240–1241). Compound 5 is isolated by column chromatography using a 1×"16" column containing 20 g of silica gel, Merck grade 9385, 230–400 mesh, and eluted with a gradient of 1% ether in hexanes to 5% ether in hexanes, used iodine as the visual indicator thereof and is typically obtained in 13% overall yield and characterized by $^1$H NMR and $^{13}$C NMR.

Polymerization of Carbamate-Derivatized Polymer

Compound 5 is polymerized in a two-step process developed by Marsella et al. (1997, Angew. Chem. Intl. Ed. Engl. 36: 1101–1103). Compound 5 is first converted to a macrocyclic intermediate by template-directed ring-closing metathesis chemistry, then the macrocyclic intermediate is polymerized by ring-opening polymerization (ROMP) to produce a polymer of high molecular weight and viscosity (as described in Ivin & Mol, 1997, Olefin Methathesis and Metathesis Polymerization, Academic Press: San Diego). High molecular weight polymer is obtained by performing the reaction in a concentrated solution of monomer and the absence of metal ions (Marsella et al., 1997, ibid.). The polymer is characterized by $^1$H NMR and $^{13}$C NMR and gel-permeation chromatography (GPC). GPC is used to determine the polymer's average molecular weight (Mw), the number average molecular weight (Mn) and the polydispersity number (Mw/Mn).

The advantage of producing Compound 6 by ROMP instead of more conventional polymerization methods, such as acyclic-diene metasynthesis (ADMET) is that the ROMP reaction proceeds by chain-growth polymerization (so-called "living" polymerization), which gives high molecular weight polymers even if the reaction does not go to completion. By comparison, ADMET polymerization is a condensation-type polymerization that requires very high conversion percentages (>99%) of the starting materials in order to produce high molecular weight polymers (as disclosed in Marsella et al., 1997, ibid.; Ivin & Mol, 1997, ibid.).

Preparation of Microparticles for Polymer Coating

Biodegradable polyacryl-starch microparticles having an average diameter of 1–2 microns are prepared as disclosed in Borissova et al. (1995, *J. Pharm. Sci.* 84: 256–262) and Stjarnkvist et al. (1991, *J. Pharm. Sci.* 80: 436–440) and are used as the vehicle to deliver INH analogs to infected macrophages. These microparticles are ideal for human use because the polyacryl-starch polymers are not immunogenic in humans (Artursson et al., 1986, *J. Pharm. Sci* 75: 697–701). In a modification of the published microparticle preparation procedure, the INH analog (0.1% by weight) described in Example 8 is dissolved in the polymer solution before precipitating the polyacryl-starch polymer into 1–2 micron microparticles. A solution of polyacryl starch (1 wt % in acetone) containing 0.1 wt % of INH analog is forced through a 100 micron aperture using 75 psi of backpressure. The polymer is sprayed into a rapidly stirring solution of 25% water in ethanol. The microparticles formed thereby are filtered and dried under high vacuum for 12 hr. The yield of the microparticles isolated in this way is typically 27% isolated yield.

Coating Microparticles with Urease-Cleavable Polymer

The carbamate-derivatized polymer prepared above is dissolved in acetone by continuous stirring for 30 minutes to give a 5 wt/v % solution. Triethyl citrate (20wt/wt % of polymer) is added as a plasticizer. Purified talc (25 wt/wt %) is added to the clear solution. Enteric coating of the INH analog-impregnated microparticles is carried out using a Uni-Glatt® Air Technologies Inc. (Ramsey, N.J.) fluid bed coater. The coating polymer is sprayed by the bottom-spraying technique using a Wurster column. The inlet and outlet air temperatures are maintained at 30° C. and 40° C. respectively. The microparticles are isolated and used without further purification.

EXAMPLE 10

Antibiotic compounds of the invention are used as follows. The microparticles of the invention as described in the Examples above or negative control (saline) are administered to an animal infected with a tuberculosis-causing microbial pathogen using both optimal and suboptimal dosages and the most appropriate route of administration. After an optimal time period (determined from the nature of the infection), phagocytic cells are collected from the animal and tested for infection with the tuberculosis-causing microbial pathogen. Phagocytic cells from peripheral blood or thoracic washings are isolated using conventional methods (Ficoll-Hypaque density gradient centrifugation) and tested for the presence of infectious tuberculosis-causing microbial pathogens using conventional immunological, microbiological and biochemical testing protocols (see *Laboratory Test Handbook*, Jacobs et al., eds., Lexi-Comp, Inc: Cleveland, Ohio, 1994; *Clinical Laboratory Medicine*, McClatchey, ed., Williams & Wiklins: Baltimore, Md., 1994; *Clinical Diagnosis and Management by Laboratory,* 18th Ed., J. B. Henry, ed., W. B. Saunders: Philadelphia, 1991).

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter comprising an activated antibiotic, antimicrobial or antiviral compound, a nonporous microparticle, and a coating material, wherein the antibiotic, antimicrobial or antiviral activity of the compound requires modification in vivo by an enzymatic or chemical activity specific for infected cells and resistance to said compound is mediated by inactivation of said enzymatic or chemical activity, whereby the compound is activated in vitro by chemically modifying the compound to overcome resistance thereto, wherein the nonporous microparticle is coated with the compound and said coated microparticle is further coated with the coating material, and wherein the coating material is specifically degraded inside a phagocytic mammalian cell infected with a microorganism to allow release of the compound within the infected cell.

2. The composition of matter of claim 1 wherein the microorganism is a tuberculosis-causing microorganism and the compound is selected from the group consisting of activated species of isoniazid, rifampin, capreomycin, ethionamide, cycloserine, ciprofloxacin, amikacin, streptomycin, ethambutol, pyrazinamide, and inhibitors of long-chain enol acyl carrier protein reductase.

3. A composition of matter according to claim 2 wherein the coating material is chemically degraded inside a mammalian phagocytic cell infected with a tuberculosis-causing microorganism.

4. A composition of matter according to claim 2 wherein the coating material is a substrate for a protein having an enzymatic activity, said protein being produced only in a mammalian cell infected with a tuberculosis-causing microorganism.

5. The composition of matter of claim 4 wherein the coating material is a substrate for a protein produced by the infected mammalian cell.

6. The composition of matter of claim 4 wherein the organic coating material is a substrate for a protein produced by the tuberculosis-causing microorganism infecting the infected mammalian cell.

7. A method of killing a microorganism infecting a mammalian cell, the method comprising contacting said cell with the composition of claim 1.

8. A method of killing a tuberculosis-causing microorganism infecting a mammalian cell, the method comprising contacting said cell with the composition of claim 2.

9. A method for treating a microbial infection in a human wherein the infecting microbe is present inside a phagocytic cell in the human, the method comprising administering a therapeutically effective amount of the composition of claim 1 to the human in a pharmaceutically acceptable carrier.

10. A method for treating a microbial infection in a human wherein the infecting microbe is a tuberculosis-causing microorganism and is present inside a phagocytic cell in the human, the method comprising administering a therapeutically effective amount of the composition of claim 2 to the human in a pharmaceutically acceptable carrier.

11. A pharmaceutical composition comprising the composition of matter of claim 1 in a pharmaceutically acceptable carrier.

12. A pharmaceutical composition comprising the composition of matter of claim 2 in a pharmaceutically acceptable carrier.

* * * * *

UNITED STATES PATENT AND TRADEMARK OFFICE
CERTIFICATE OF CORRECTION

PATENT NO. : 6,455,073 B1
DATED : September 24, 2002
INVENTOR(S) : Michael J. Meredith, Milton B. Yatvin and Richard L. Pederson It is certified that error appears in the above-identified patent and that said Letters Patent is hereby corrected as shown below:

<u>Drawings,</u>
Sheet 2, Fig. 2 should appear as follows:

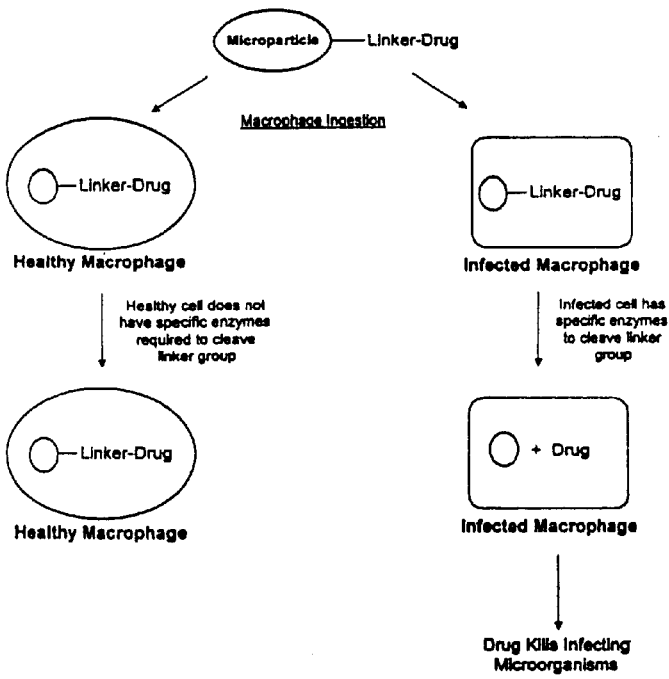

Figure 3:
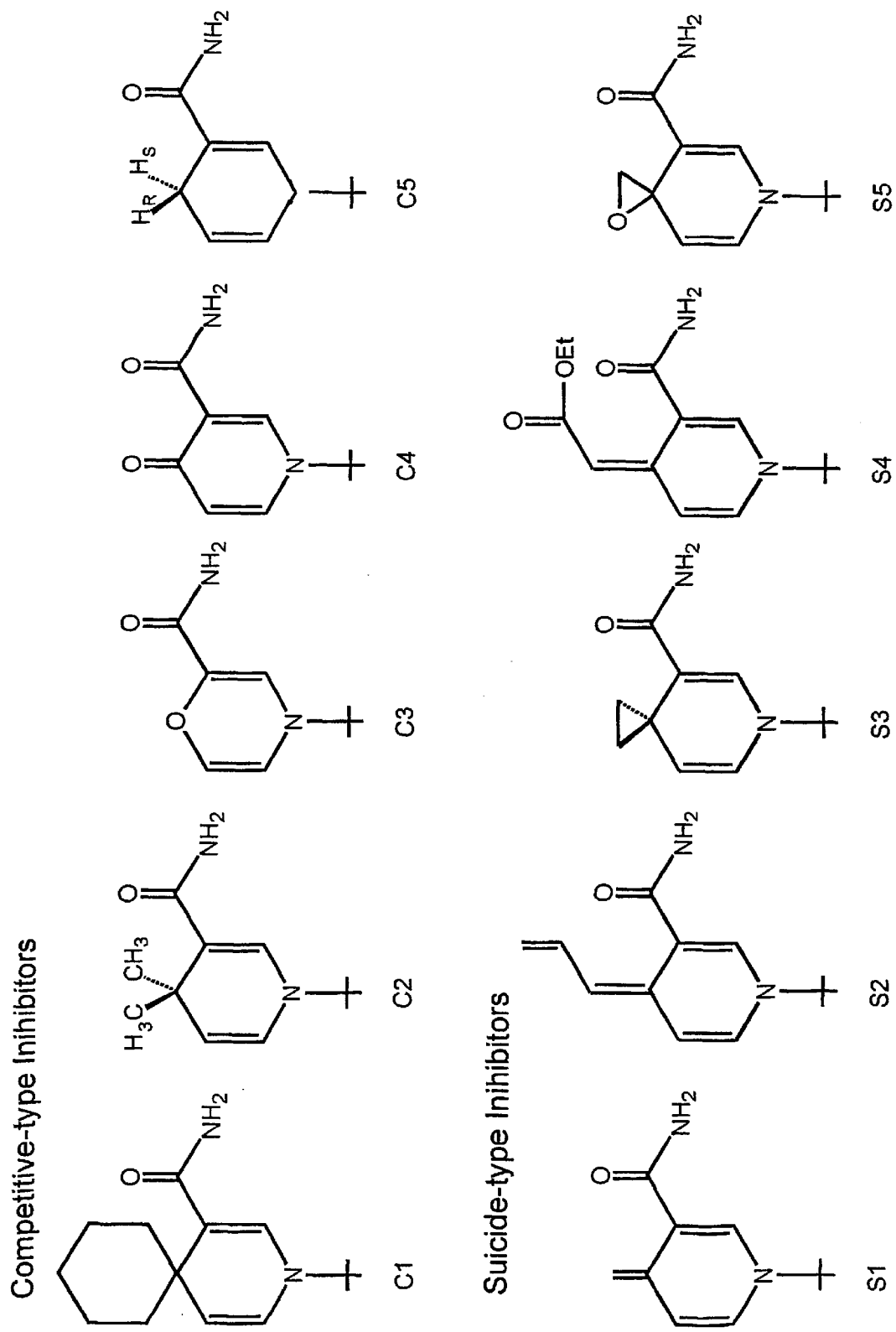
FIG. 3 depicts the synthetic scheme put forth in Example 1.
Figure 4A:
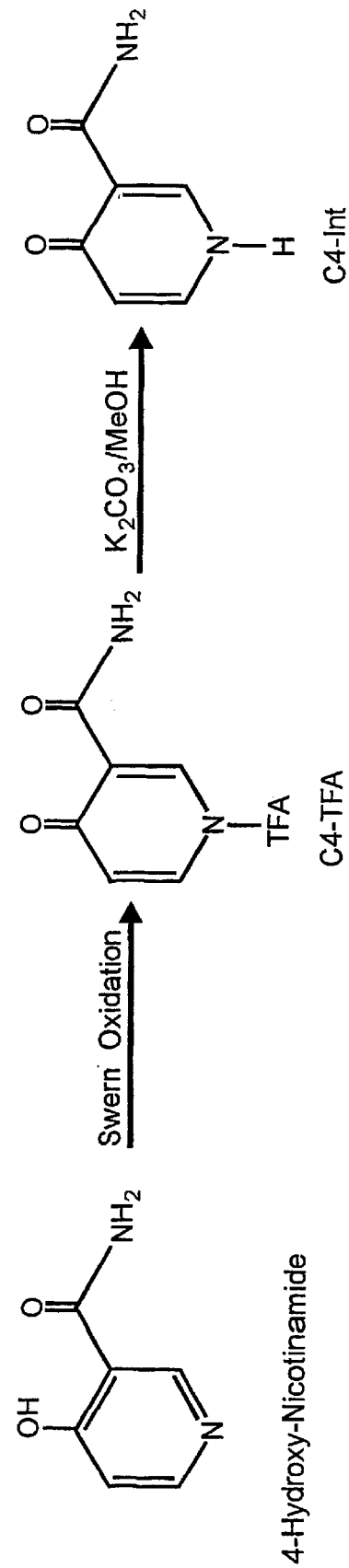
FIG. 4 shows a synthetic scheme for producing a soluble dye-linked compound as set forth in Example 1.
Figure 4B:
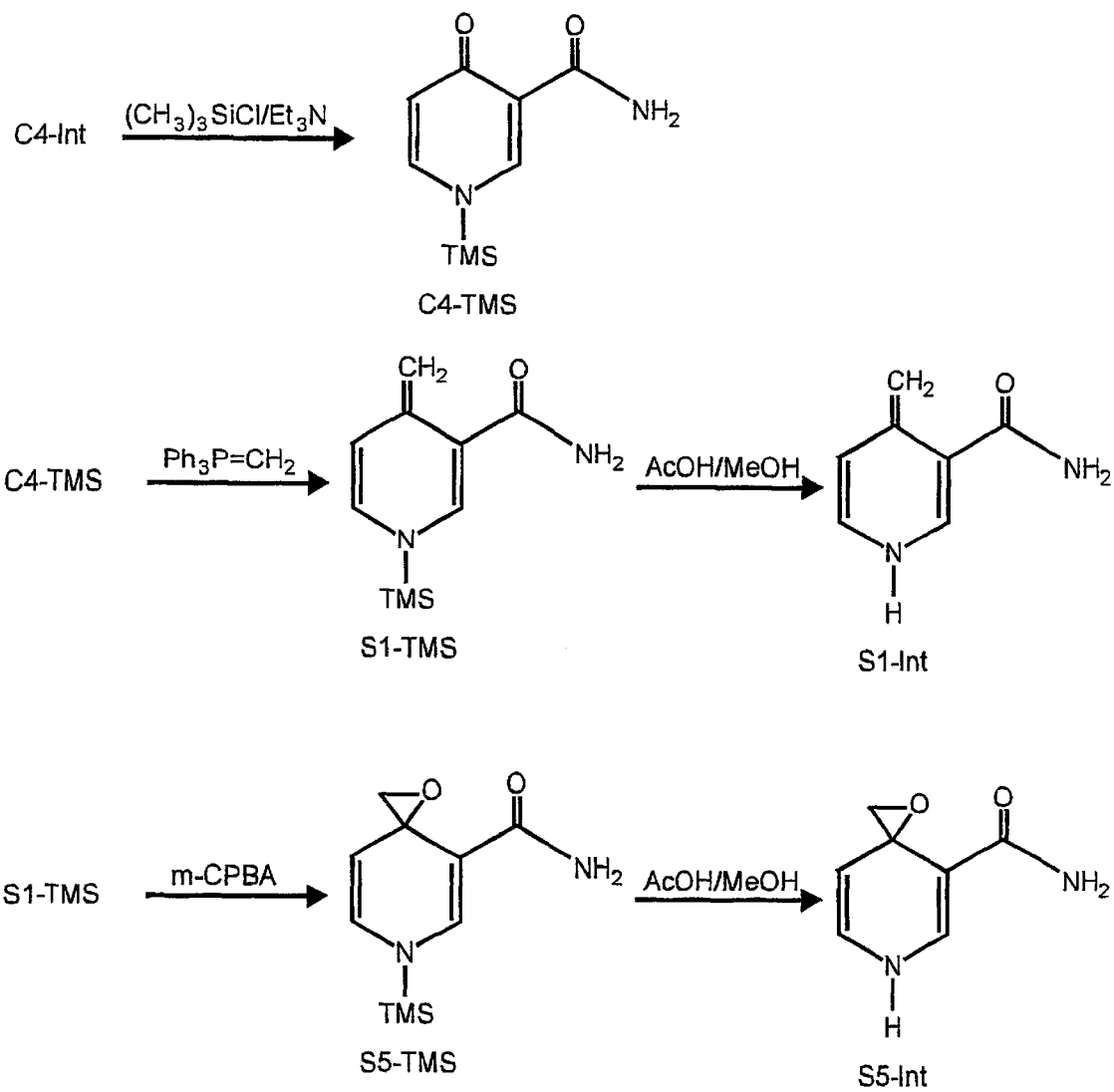
Figure 4C:
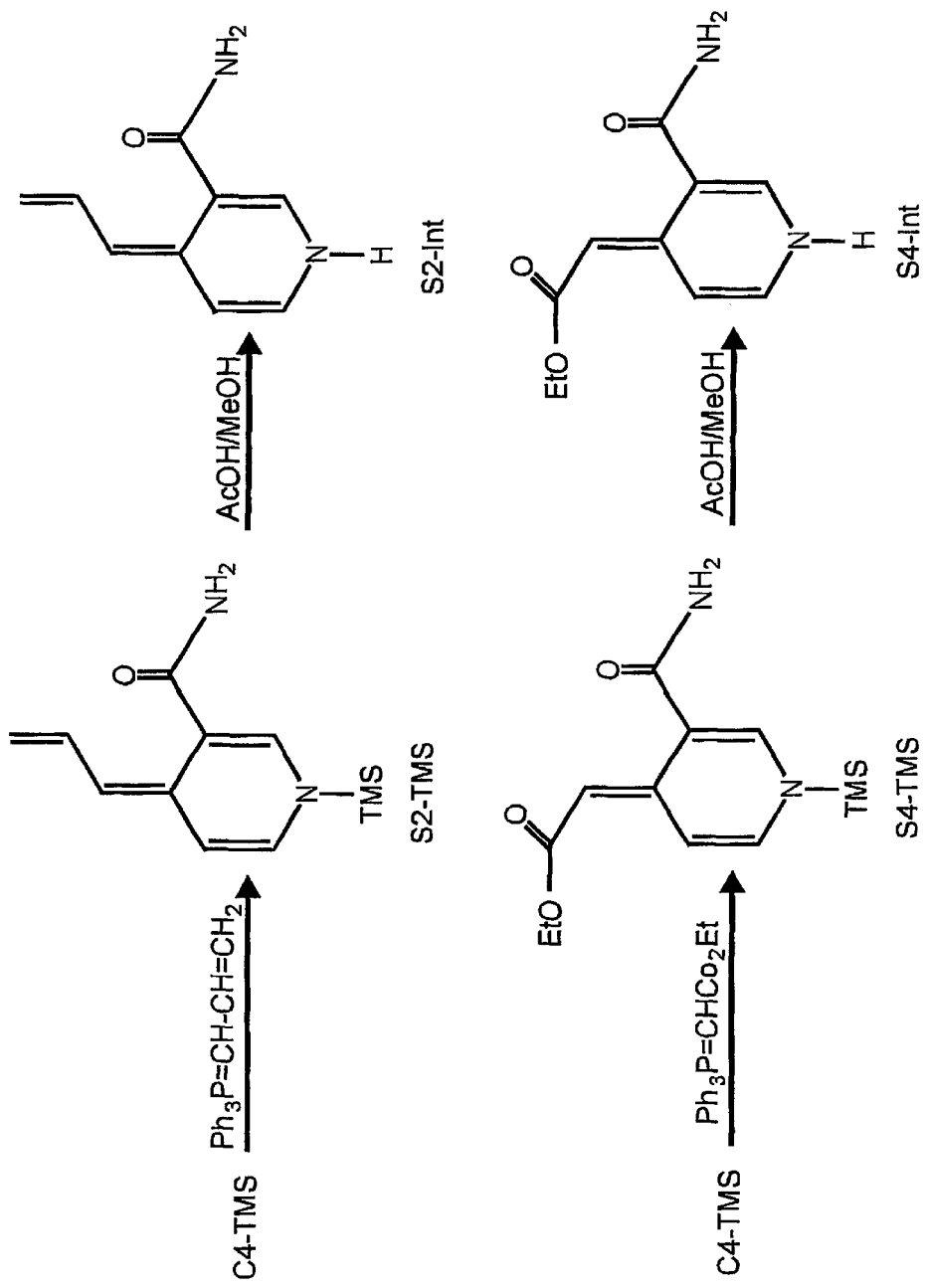
Figure 4D:
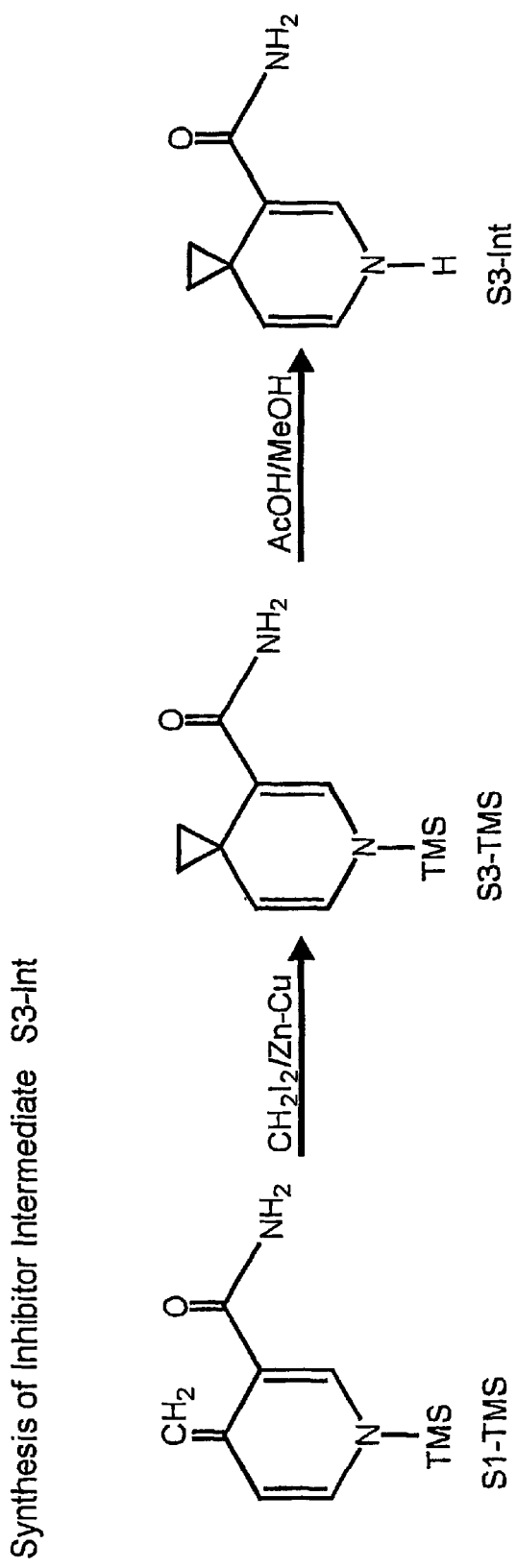
Figure 4E:
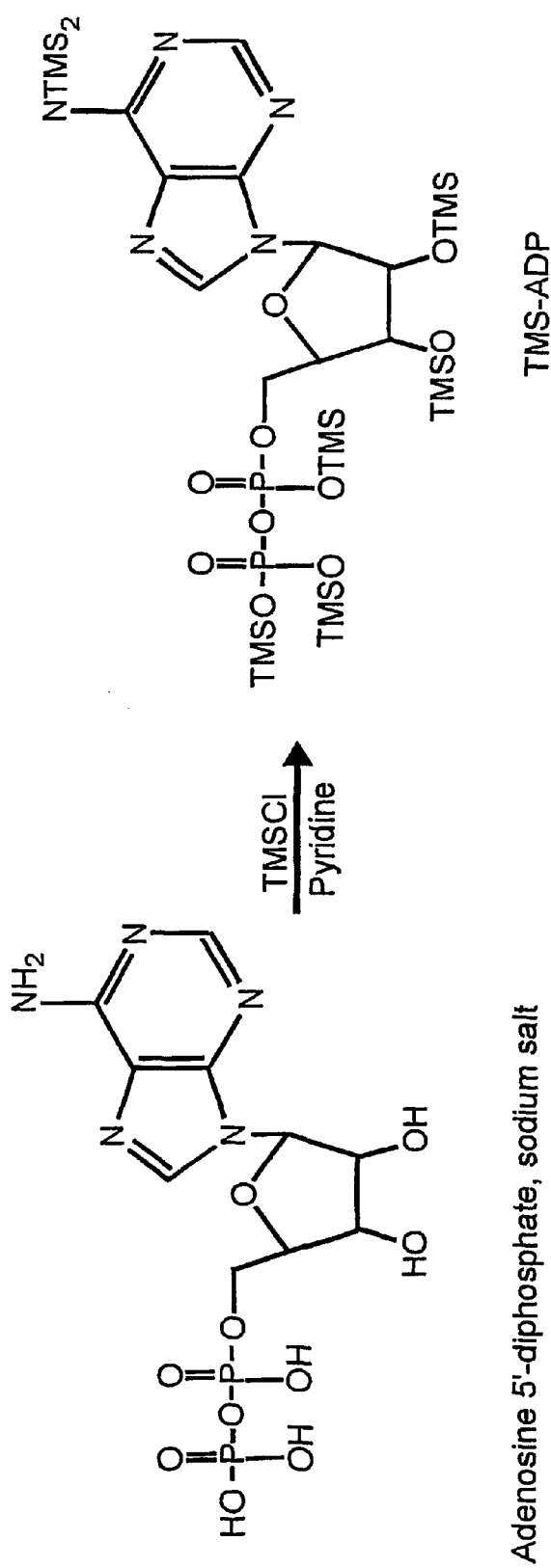
Figure 4F:
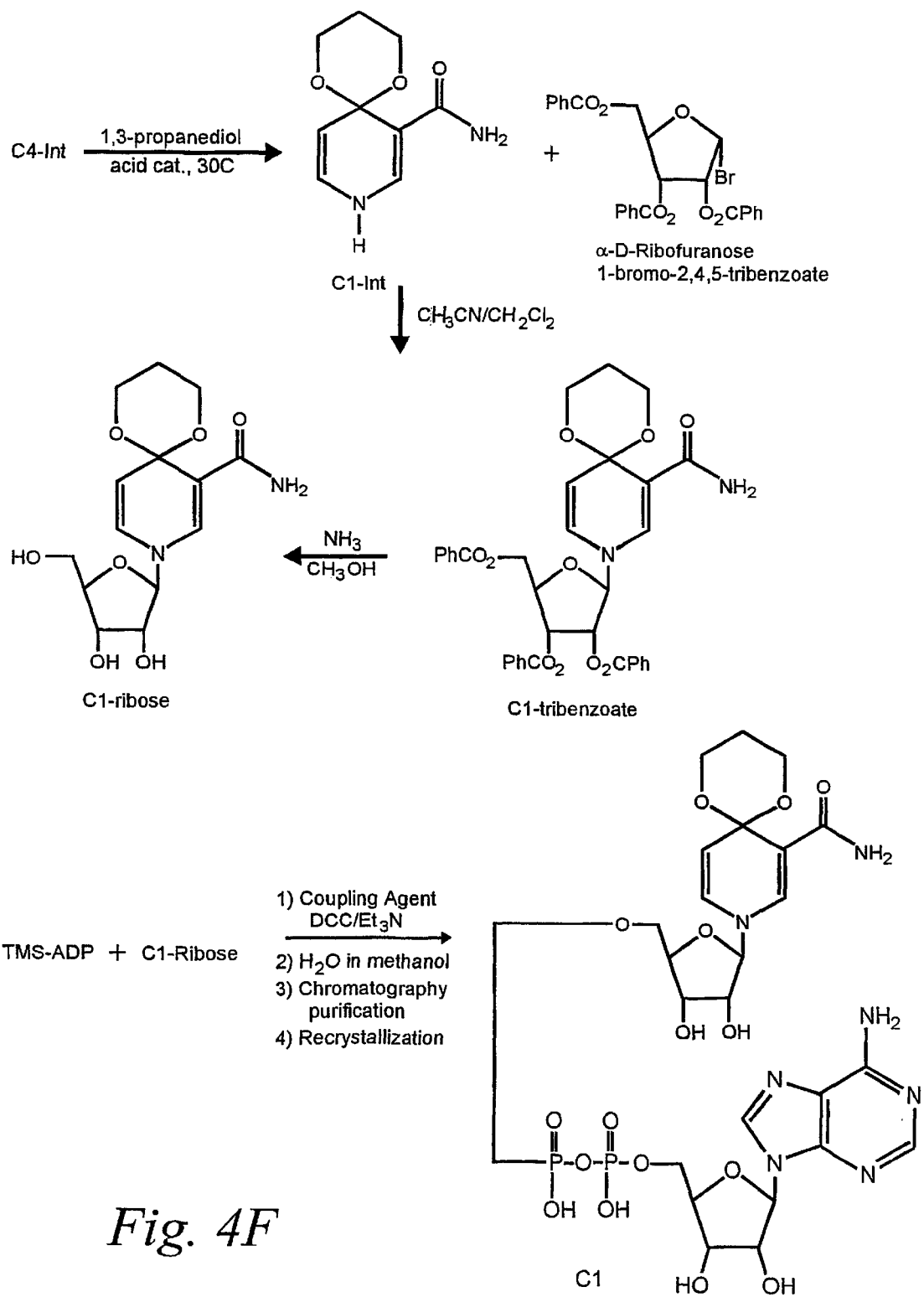
Figure 4G:
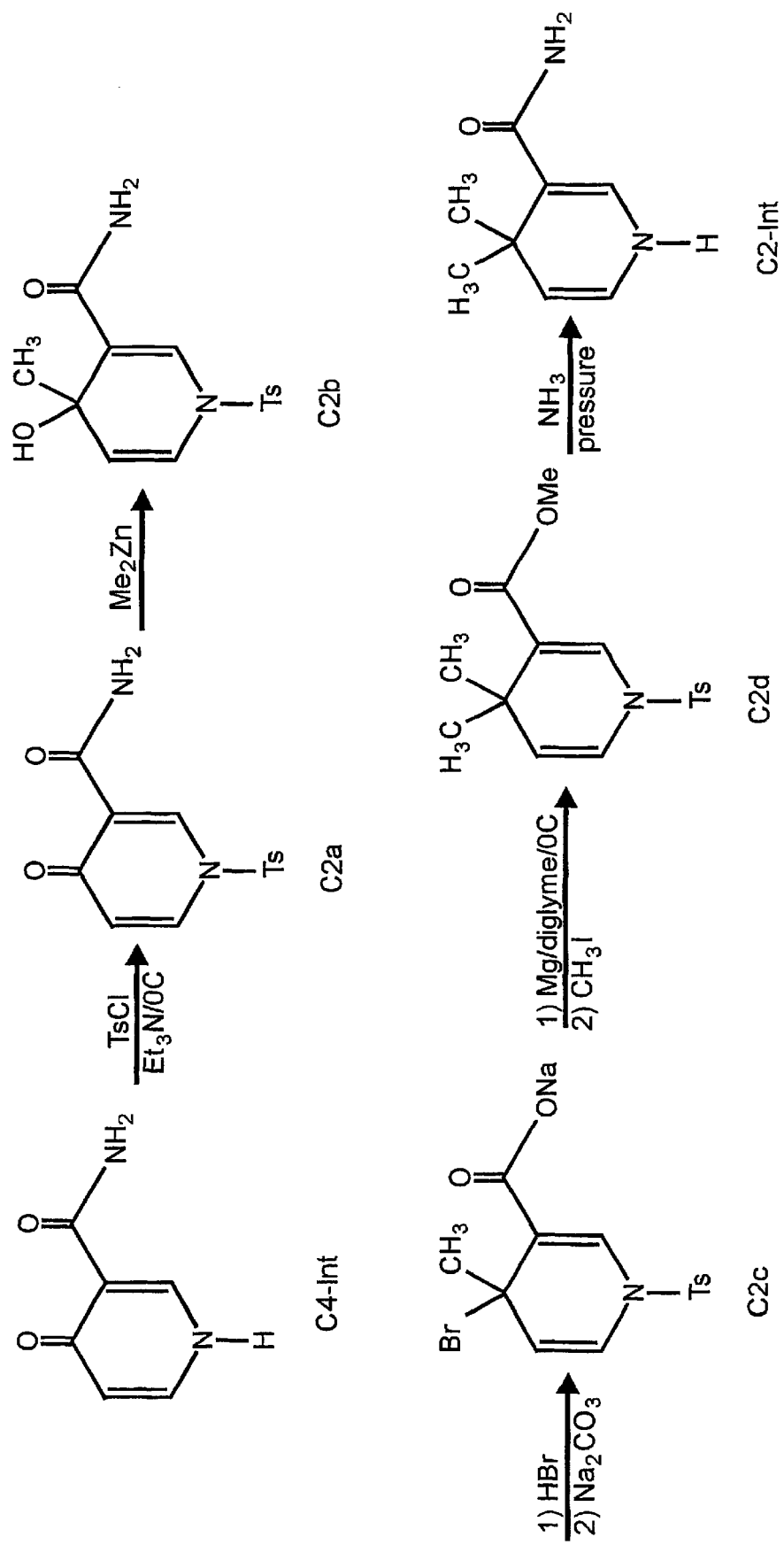
Figure 4H:
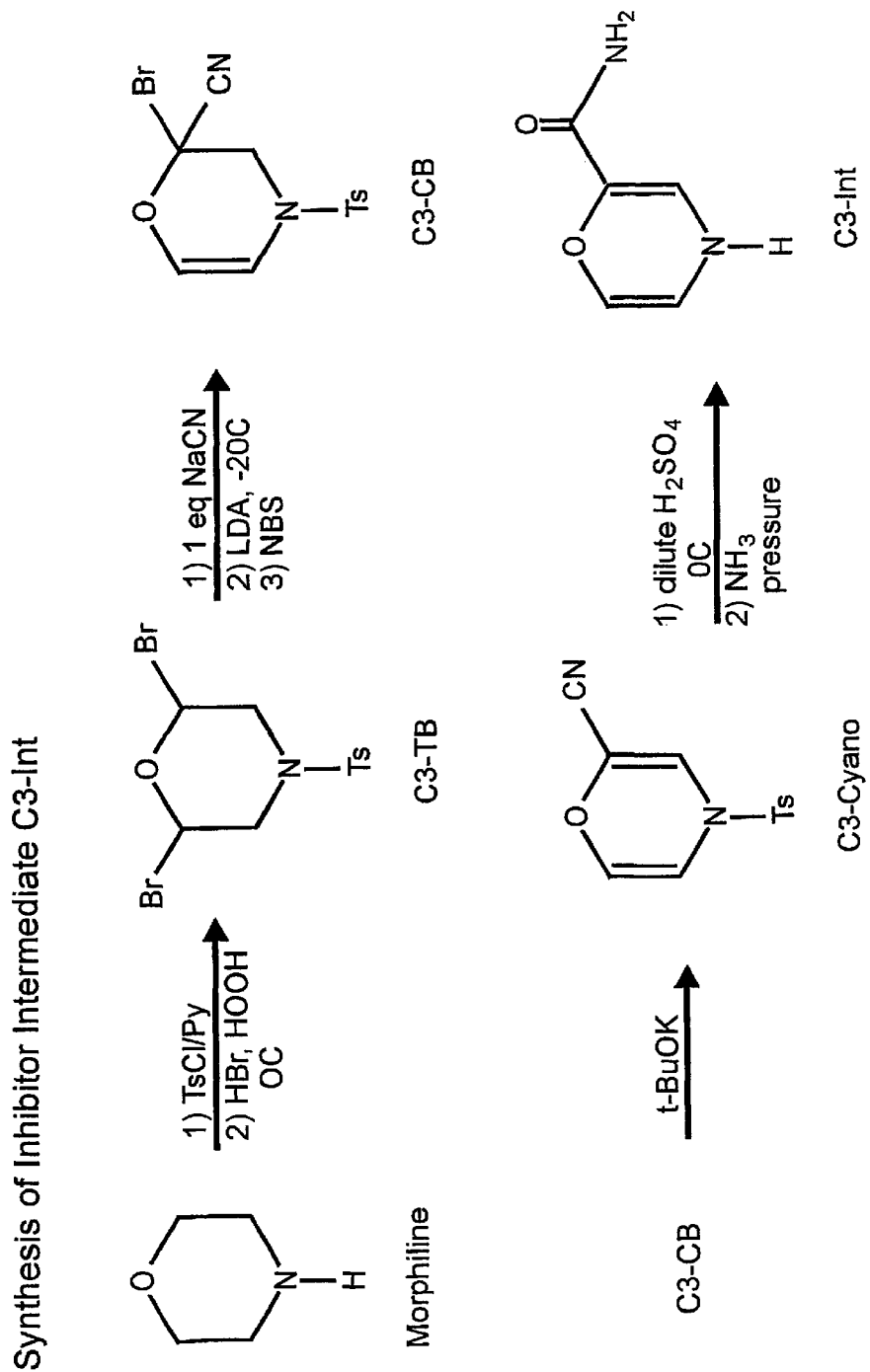
Figure 4I:
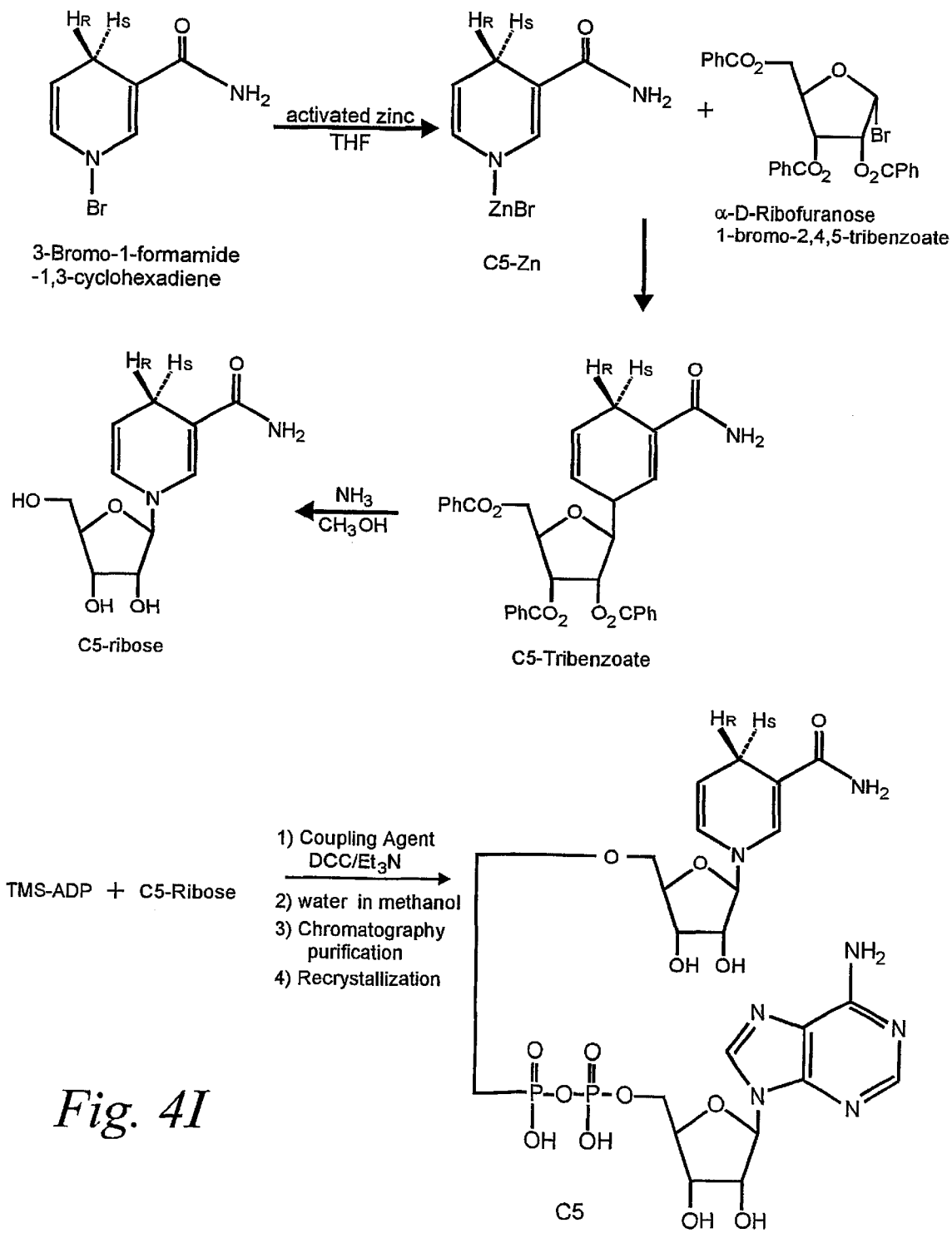
Figure 4J:
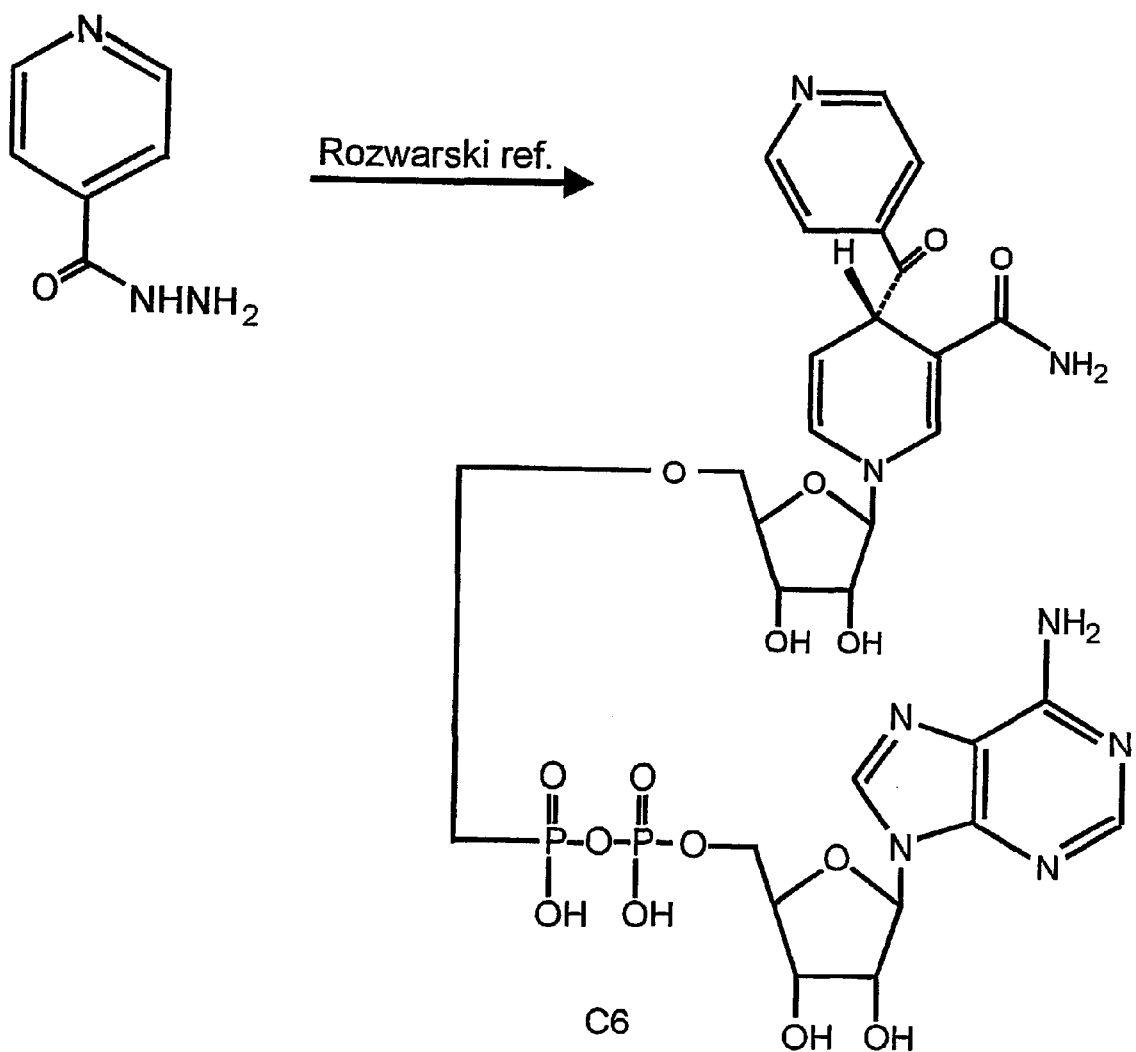
Figure 5:
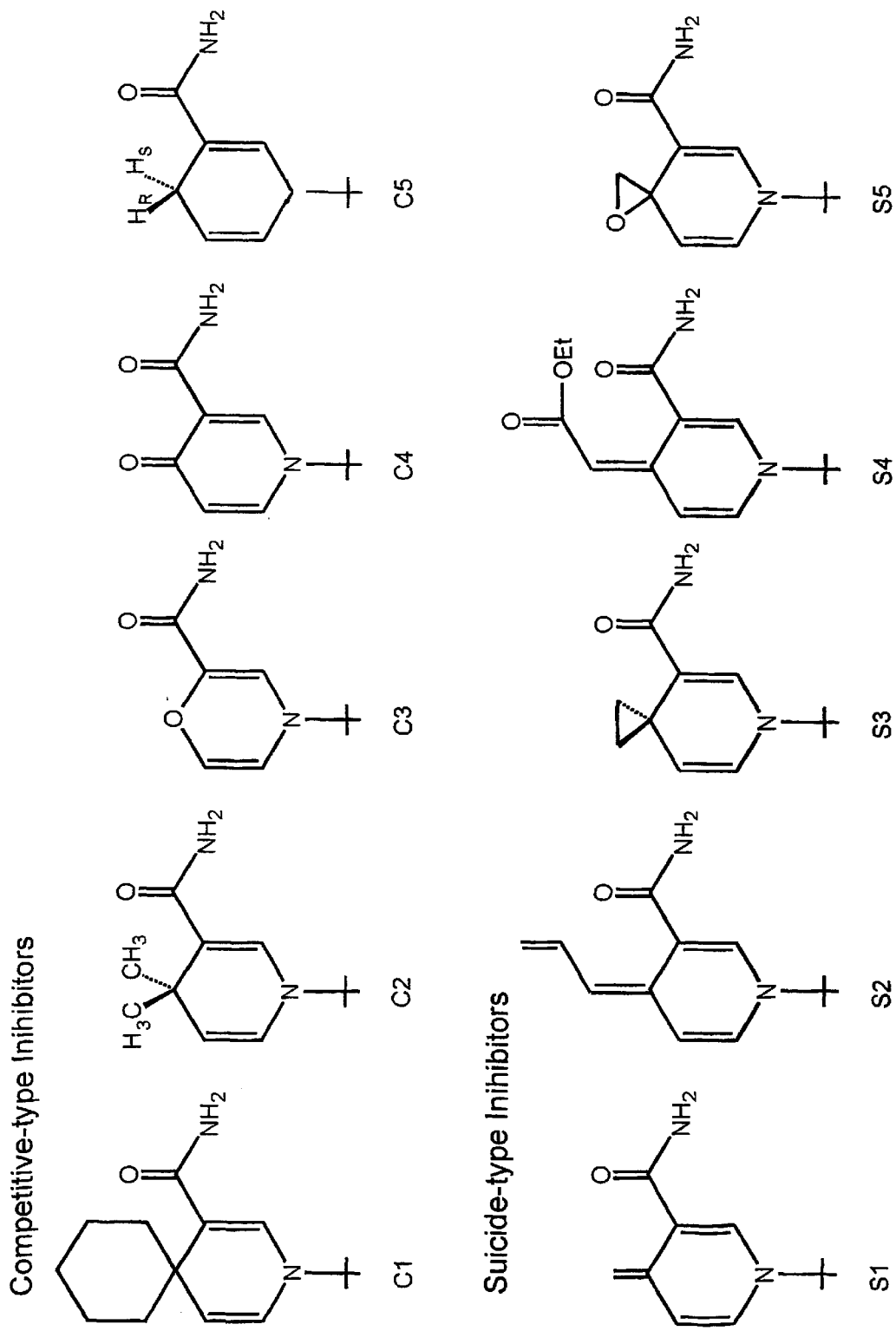
FIG. 5 depicts competitive and suicide substrates of InhA.
Figure 6:
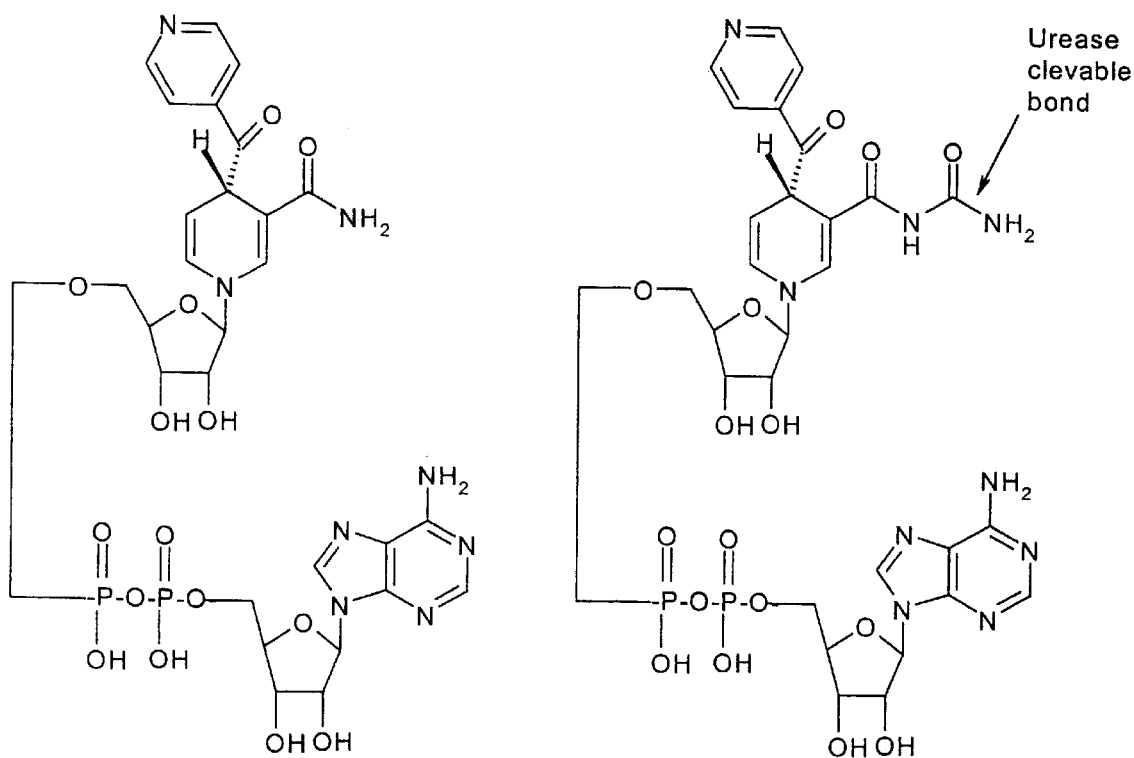
FIG. 6 depicts INA inactivated by covalent modification with a urea moiety.
Figure 7:
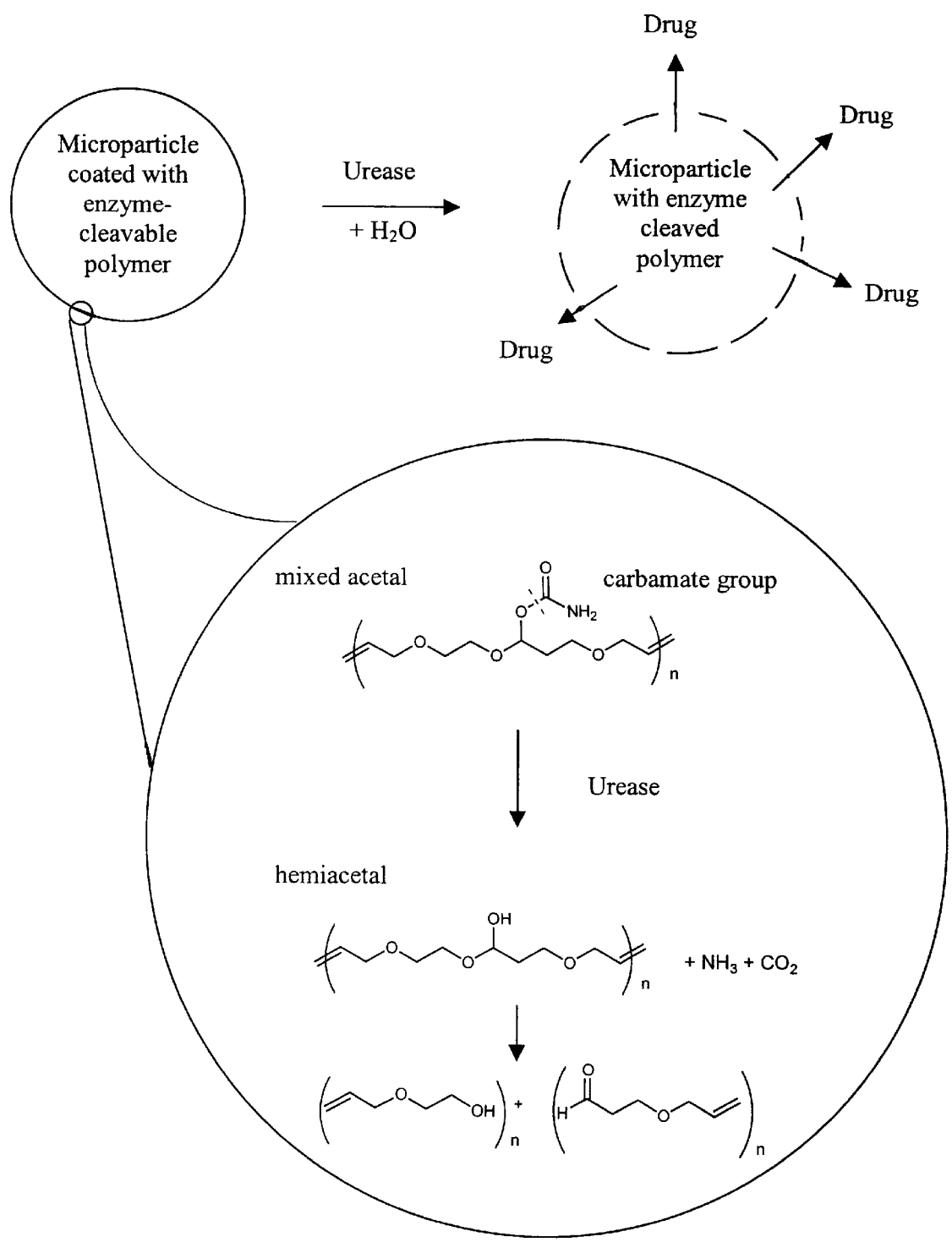
FIG. 7 is a schematic diagram of urease-catalyzed cleavage of the carbamate-containing polymer described in Example 9.
Figure 8:
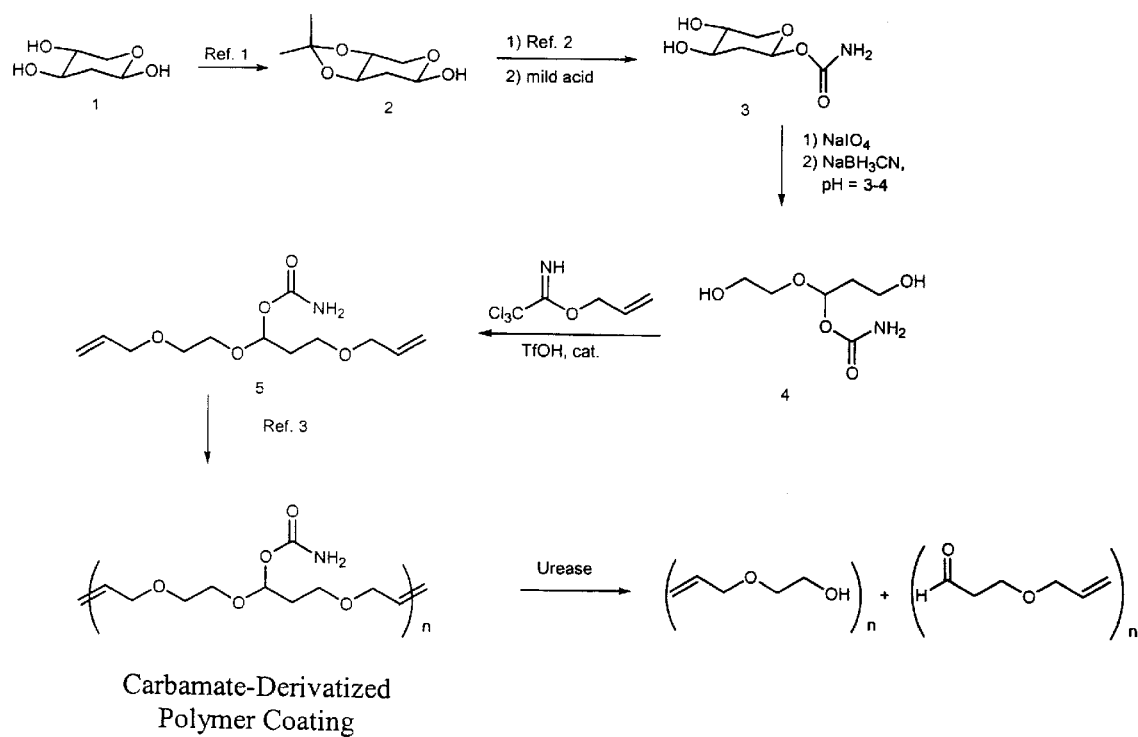
FIG. 8 shows a synthetic scheme for producing a urease-catalyzed cleavage of the carbamate-containing polymer described in Example 9.

Sheet 3, Fig. 3 should appear as follows:

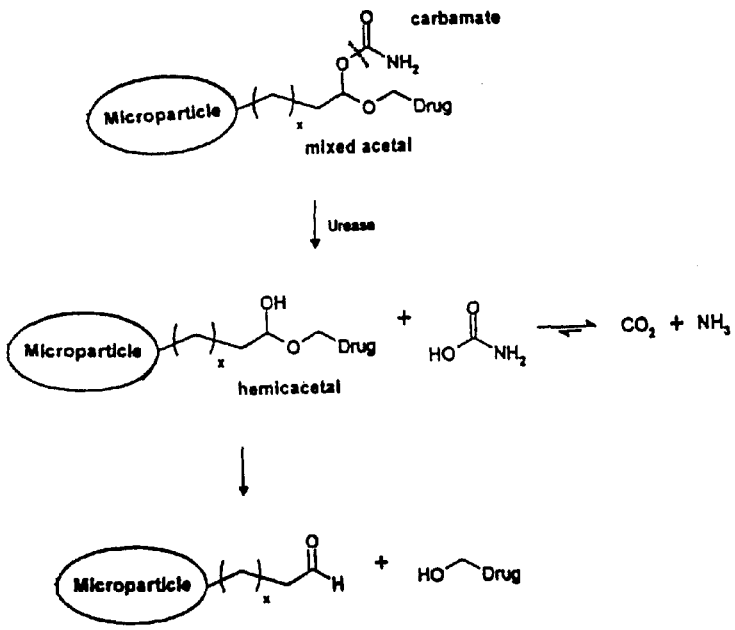

UNITED STATES PATENT AND TRADEMARK OFFICE
CERTIFICATE OF CORRECTION

PATENT NO. : 6,455,073 B1
DATED : September 24, 2002
INVENTOR(S) : Michael J. Meredith, Milton B. Yatvin and Richard L. Pederson It is certified that error appears in the above-identified patent and that said Letters Patent is hereby corrected as shown below:

Sheets 4-13, Figures 4A-4J, Fig. 4 should appear as follows:

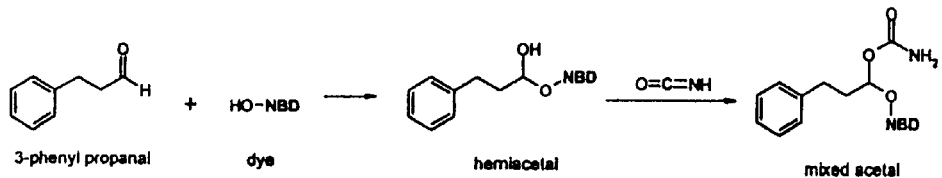

Figure 4. Route for Synthesis of Mixed Acetal of NBD and Urease-Cleavable Carbamate Signed and Sealed this Thirtieth Day of December, 2003

JAMES E. ROGAN
*Director of the United States Patent and Trademark Office*